United States Patent
Mahe

(10) Patent No.: US 7,680,319 B2
(45) Date of Patent: Mar. 16, 2010

(54) METHOD FOR THE NON-DESTRUCTIVE TESTING OF AN ELEMENT FOR A NUCLEAR REACTOR

(75) Inventor: Philippe Mahe, Montmiral (FR)

(73) Assignee: Societe Franco-Belge de Fabrication de Combustible, Courbevoie (FR)

( * ) Notice: Subject to any disclaimer, the term of this patent is extended or adjusted under 35 U.S.C. 154(b) by 651 days.

(21) Appl. No.: 10/580,513

(22) PCT Filed: Nov. 10, 2004

(86) PCT No.: PCT/FR2004/002895

§ 371 (c)(1),
(2), (4) Date: Feb. 26, 2007

(87) PCT Pub. No.: WO2005/062313

PCT Pub. Date: Jul. 7, 2005

(65) Prior Publication Data

US 2007/0248239 A1    Oct. 25, 2007

(30) Foreign Application Priority Data

Nov. 24, 2003   (FR) ................... 03 13754

(51) Int. Cl.
*G06K 9/00*   (2006.01)
*G21C 17/00*   (2006.01)
*H01L 27/146*   (2006.01)

(52) U.S. Cl. ............... 382/141; 382/100; 376/249; 250/370.09

(58) Field of Classification Search ............... 382/100, 382/249, 118, 232, 248, 276, 286, 291, 154, 382/181, 190, 195, 203; 250/370.08, 370.09; 376/178, 245, 251, 153, 156; 358/1.9, 1.1, 358/500, 501, 502, 518, 520, 1.18
See application file for complete search history.

(56) References Cited

U.S. PATENT DOCUMENTS

| 5,999,636 | A | 12/1999 | Juang |
| 6,154,561 | A | 11/2000 | Pratt et al. |
| 2001/0055415 | A1 | 12/2001 | Nozaki |

FOREIGN PATENT DOCUMENTS

| DE | 3809221 | 9/1989 |
| EP | 0 597 639 | 5/1994 |
| WO | WO 97/16921 | 5/1997 |

OTHER PUBLICATIONS

Patent Abstracts of Japan, JP 2000249785, Sep. 14, 2000; vol. 2000, No. 12, Mitsubushi Nuclear Fuel Co. Ltd., "Inspecting Method and System for Atomic Nuclear Fuel Rod".
"Image Analysis and Mathematical Morphology", Ac. Press, vol. 1 (1982), vol. 2 (1988).
Jourlin and Pinoli, "A Model for logarithmic image processing", J. of Microscopy, vol. 149, Pt 1, Jan. 1988, pp. 21-35.

*Primary Examiner*—Sheela C Chawan
(74) *Attorney, Agent, or Firm*—Davidson, Davidson & Kappel, LLC

(57) ABSTRACT

A method for the non-destructive testing of an element for a nuclear reactor having the steps of: a) acquiring a radiographic digital image of at least one area in element, b) creating a reference image through the digital processing of the image obtained, and c) comparing the image obtained, processed if necessary, with the reference image to detect the presence of defects.

32 Claims, 22 Drawing Sheets

METHOD FOR THE NON-DESTRUCTIVE TESTING OF AN ELEMENT FOR A NUCLEAR REACTOR

FIELD OF THE INVENTION

The invention relates to a method for the non-destructive testing of an element for a nuclear reactor. The invention applies in particular to the testing of nuclear fuel rod assemblies used in pressurised water reactors.

BACKGROUND INFORMATION

Generally, nuclear rods comprise a tubular sheath containing pellets of nuclear fuel which is sealed at its extremities by a bottom plug and a top plug. These plugs are welded to the sheath by circular weld beads ensuring a seal between the sheath and the plugs.

In addition to this, the upper plug has a channel for filling the sheath with a pressurized inert gas, for example helium. When the fuel rods have been manufactured, this channel is leaktightly sealed by a spot weld. The circular weld beads may show various types of defects. Thus, porosity may be present. This comprises voids in the weld bead. The weld beads may also show lack of penetration, that is to say parts where the radial extent of the beads is less than desired.

Where a TIG (Tungsten Inert Gas) welding method is used, the weld beads may also have tungsten inclusions. The latter type of defect may also be observed in the spot weld plugging the filling channel.

In addition to this, it may happen that this spot weld is in a position and of such a size that it does not satisfactorily block the filling channel. Lack of penetration in the weld bead and poor positioning of the spot weld are likely to give rise to leaks in the fuel rod and therefore to the release of radioactive particles or gases into the nuclear reactor's primary circuit. Porosities and inclusions have an adverse effect on the mechanical integrity of the rod. These defects have to be avoided and for this reason non-destructive testing procedures are applied to the manufactured fuel rods.

In order to check the quality of the weld beads and the sealing spot welds a digital radiographic image of the corresponding areas of rods undergoing inspection is acquired.

The image acquired is then compared with a stored reference image. This reference image has been obtained from a fuel rod which is considered to be free from any defects. The reference image is therefore subtracted from the image obtained, and then the resulting image is digitally processed in order to cause any defects to appear more clearly, and an overall score is allocated to the weld bead, one score for the sealing spot weld and one score for tungsten inclusions. Beyond threshold values, the rod is considered to be non-conforming.

Because of uncertainties in the positioning of the rods and manufacturing tolerances, the position of a rod and its dimensions on the image obtained differ from those of the rod in the reference image. This therefore means that complex processing of the image obtained by subtraction is required in order to be able to detect any manufacturing defects. Furthermore, it has been found that the reliability of this check has remained low, despite this processing of the image obtained by subtraction, which has made it necessary to reject a large number of rods as being non-conforming in order to be on the safe side.

One objective of the invention is to solve this problem by providing a more reliable method for the non-destructive testing of an element for a nuclear reactor.

With this aim the objective of the invention is a method for the non-destructive inspection of an element for a nuclear reactor, a method comprising the steps of:

a) acquiring a digital radiographic image of at least one area of the element,
b) creating a reference image by digital processing of the image obtained, and
c) comparing the image obtained, which may have been processed, with the reference image to detect the presence of any defects.

In accordance with particular embodiments, the method may comprise one or more of the following features taken in isolation or in any technically possible combination:

- the element is part of a nuclear fuel assembly,
- the element is a nuclear fuel rod extending along a longitudinal axis and comprising a sheath sealed off by top and bottom plugs and containing a nuclear fuel,
- the area comprises the weld bead between one of the plugs and the sheath,
- the area comprises a spot weld sealing a channel passing through a plug,
- step b) comprises a substep b1) of opening or closing the image by the addition of a structuring element,
- the structuring element has an elongated shape along the longitudinal axis of the rod,
- the structuring element is a segment of p pixels, p being a whole number which is not zero,
- a defect which has to be detected is porosity or lack of penetration in the weld bead, and substep b1) is a substep of opening the image by addition of the structuring element,
- a defect which has to be detected is a tungsten inclusion, and substep b1) is a substep of closing the image by addition of the structuring element,
- step b) comprises a substep b0) of smoothing the image through a convolver, prior to substep b1),
- the convolver is a square of side n pixels, n being a whole number which is not zero,
- step c) comprises a substep c1) of calculating the difference between the image obtained, processed if necessary, and the reference image, and dividing that difference by the image obtained, processed if necessary, or by the reference image,
- after substep c1) the method comprises a substep c2) of multiplying the image by a coefficient substantially corresponding to the maximum light intensity of the viewing device used to acquire the radiographic image,
- after substep c1) the method comprises a substep of smoothing the image through a convolver,
- the convolver is a square of side q pixels, q being a whole number,
- the convolver lies with its length transverse to the longitudinal axis,
- after substep c1) the method comprises a step of binarising the image,
- as the defect which has to be detected is a lack of seal at the spot weld, step b) comprises a substep b1) of projecting the image along the longitudinal axis and reconstructing the image from its projection along that axis,
- prior to substep b1) step b) comprises a substep b0) of smoothing the image acquired by a convolver,
- the convolver is a square of side t pixels, t being a whole number, step c) comprises a substep c1) of subtracting the reference image from the image obtained, which may have been processed, after substep c1) the method comprises a substep of binarising the image, the method comprises a step d) of automatic detection and determination of the characteristics of a region of the image produced in step c) corresponding to a defect, one of the characteristics is the position of the defect detected in the image, one of the characteristics is representative of the dimension of the defect detected, the method comprises a step d) of determining the minimum axial thickness of the spot weld, steps a) to d) are performed for several viewing angles, the method comprises a step e) of reconstructing the defects detected in the images corresponding to different viewing angles, step e) comprises a substep e1) of determining the positions which a defect detected in a first step corresponding to a first viewing angle may occupy in a second image corresponding to a second viewing angle, a substep e2) comparing the positions so determined with the positions of the defect(s) actually detected in the second image in order to determine whether the defect has been detected in the second image and if the defect has been detected in the second image, a substep e3) of calculating a dimension of the defect from the representative characteristics of the dimensions of the defect determined in the first and second images, the method comprises a step e) of summing the representative characteristics of the dimension determined for several viewing angles and comparing the sum with a threshold value in order to reach a decision on whether the element conforms with predetermined manufacturing criteria, the method comprises a step e) of calculating a mean for the minimum thicknesses determined for several viewing angles and comparing it with a threshold value in order to reach a decision on whether the element conforms with predetermined manufacturing criteria.

BRIEF DESCRIPTION OF THE DRAWINGS

The invention will be better understood from a reading of the description which follows, provided solely by way of example, and given with reference to the appendix drawings, in which.

DETAILED DESCRIPTION

Figure 1:
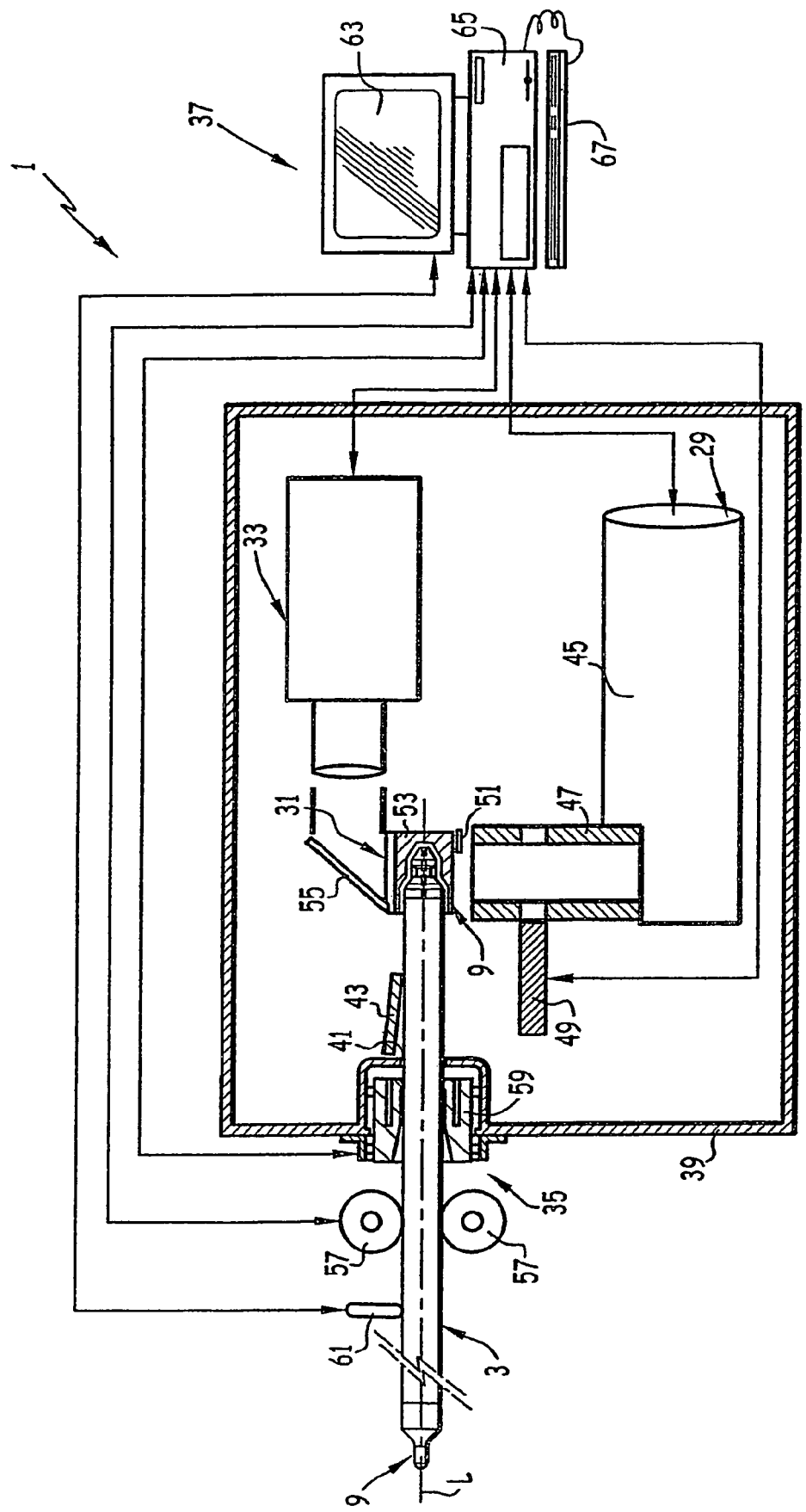
FIG. 1 is a diagrammatical view of a non-destructive testing facility for implementing the method according to the invention.

FIG. 1 diagrammatically illustrates a facility for the non-destructive testing of nuclear fuel rods 3 for pressurised water reactors.

Figure 2:
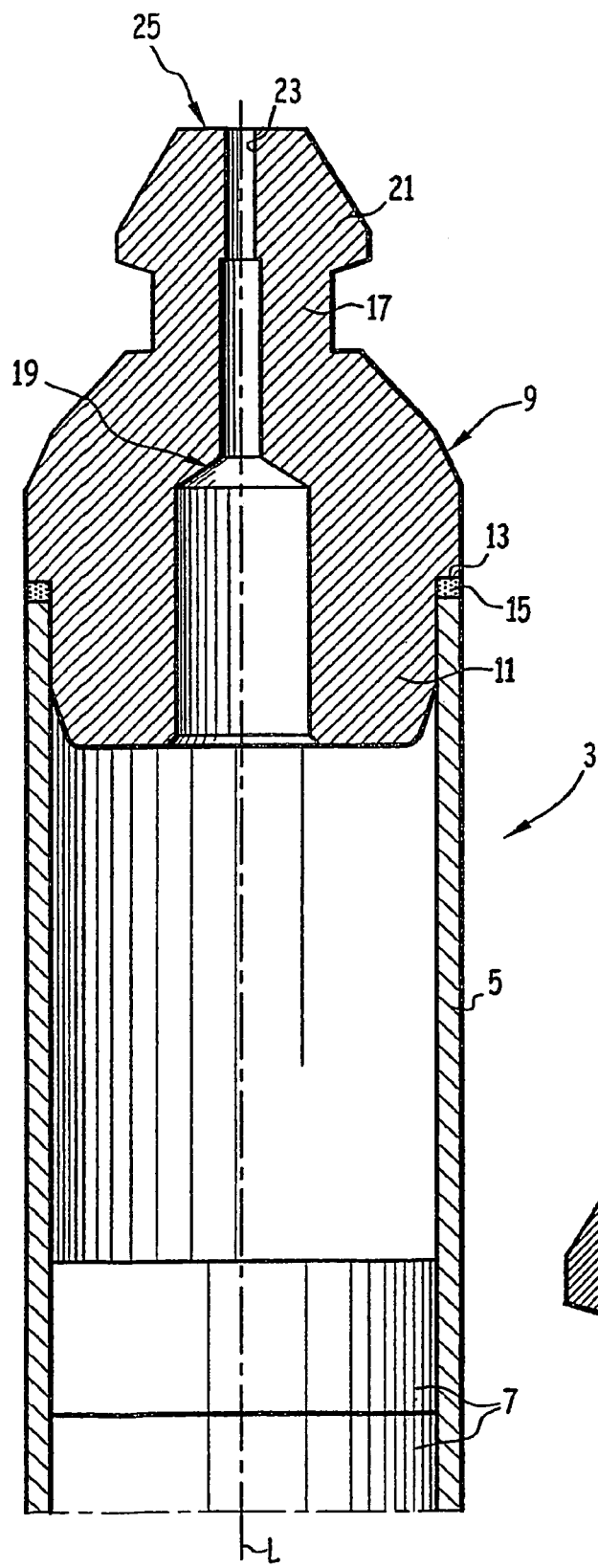
FIG. 2 is a partial view in longitudinal cross-section illustrating the upper extremity of a nuclear fuel rod before the sheath is filled with an inert gas.

As more particularly illustrated in FIG. 2, such a rod 3 extends along a longitudinal direction L and comprises a tubular sheath 5 which encloses a nuclear fuel, for example in the form of stacked pellets 7. Sheath 5 is sealed at its extremities by a top plug 9 and a bottom plug 9, which cannot be seen in FIG. 2 but is shown on the left in FIG. 1. The general structure of plugs 9 is similar and only that of top plug 9 will be described below.

Top plug 9 comprises a bottom part 11 which engages the upper extremity of sheath 5 virtually without play. This bottom part 11 is connected by a shoulder 13 to the main part of plug 9. A circular weld bead 15 extends between shoulder 13 and the upper part of sheath 5.

This bead 15 ensures that top plug 9 is leaktightly secured to sheath 5.

Plug 9 also comprises a thinner part 17 which can be seized by a grasping clamp.

Furthermore, and unlike bottom plug 9, top plug 9 has a channel 19 for filling sheath 5 with a pressurised inert gas. This channel is sometimes referred to as the pressurising channel.

Channel 19 has several successive lengths whose diameters generally decrease from part 11 which is fitted into sheath 5 towards the outer extremity 21 of plug 9.

At its top extremity or outer extremity, channel 19 has a terminal section or seal weld location 23. This section 23 opens onto the surface 25 of the top extremity of plug 9 via a circular opening whose centre is located on longitudinal axis L.

After sheath 5 has been filled with pellets 7, it is sealed off by top and bottom plugs 9 which are welded to sheath 5. It will be noted that a spring (not shown) is placed between top pellet 7 and top plug 9.

Sheath 5 is then filled with a pressurised inert gas such as helium via channel 19, and then channel 19 is leaktightly sealed in its upper section 23.

Figure 3:
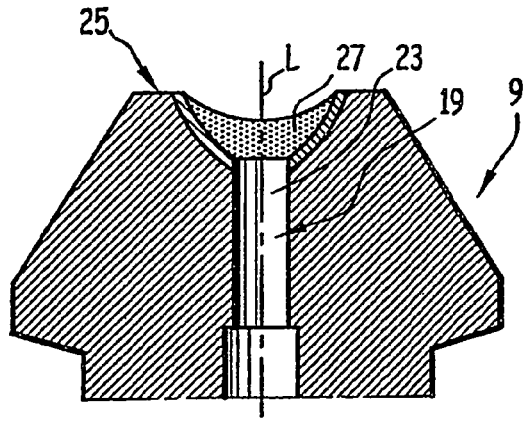
FIG. 3 is a partial magnified view in longitudinal cross-section illustrating the upper extremity of the top plug of the rod in FIG. 2 after the filling channel has been provided with a leaktight seal.

As illustrated in FIG. 3, this leaktight seal is obtained by a spot weld 27 obtained by fusing the material of plug 9 in the vicinity of upper section 23.

Returning to FIG. 1, facility 1 comprises in particular:
an X-ray source 29,
a device 31 for converting X-rays into light rays,
a device 33 for acquiring digital images,
means 35 for moving a fuel rod 3, and
a computerized system 37.

Source 29, conversion device 31 and acquisition device 33 are located within a biological protection enclosure 39 which receives the extremity of rod 3 under examination through an opening 41 which can be closed off in the absence of rod 3 by a flap 43. In FIG. 1 it is the top end of rod 3 which is inserted into enclosure 39 and which will therefore be inspected.

Source 29 comprises a tube 45 for creating X-rays and a collimator 47 to orientate the X-rays radially towards top plug 9 in which welds 15 and 27 are to be checked for potential leaks.

Source 29 also comprises a plug 49 which may be controlled like tube 45 by computerized system 37. Source 29 also comprises an image quality indicator (IQI) 51. Conventionally, this indicator comprises a plate pierced by two gauged holes. Comparison between the two dimensions of these holes and their dimensions on the image obtained makes it possible to check the quality of the image obtained.

Top plug 9 is engaged in a compensating block 53 of substantially rectangular shape and has an internal cavity of a shape which substantially matches that of the top end of rod 3 which it receives. This block 53 is for example made of a zirconium alloy.

The X-rays emerging from tube 45 pass through compensating block 53 and the upper extremity of rod 3 radially with respect to its longitudinal direction L.

The X-rays then strike device 31 which is for example a screen comprising an aluminium pellet covered with gadolinium oxysulphide doped with terbium. The X-rays are then converted into photons which are passed to image acquisition device 33 via a mirror 55.

This device 33 is for example a CCD camera.

Camera 33 is connected to computerized system 37 to provide it with the digital images acquired and in order to be controlled by the latter.

Figure 4:
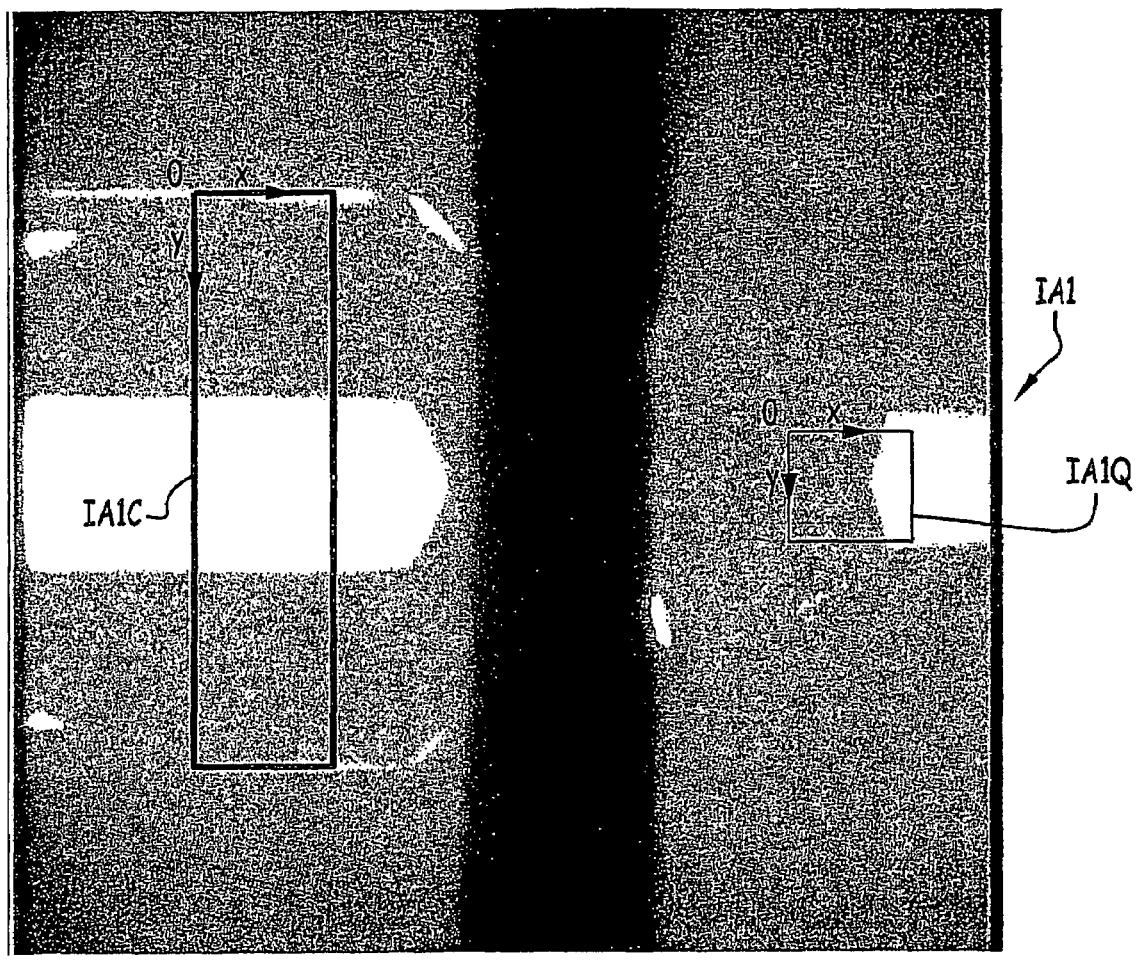
FIG. 4 illustrates an image acquired when implementing the non-destructive method of test according to the invention.

The image so acquired, IA1, is illustrated in FIG. 4. The letter A indicates that this is the image obtained and the FIG. 1 that it is the first view. The dark vertical band in the centre corresponds to a lead screen placed within compensating block 53 to diminish the great brightness which would be produced by the thin part 17 of plug 9.

A moving arrangement 35 comprises in particular motorised rollers 57 for longitudinally moving rod 3 and a rotating clamp 59 through which it can be turned about its axis L in order to acquire images from different viewing angles.

Motorized rollers 57, which are controlled by computerized system 37, can be used to cause the extremity of a rod 3 under inspection to enter enclosure 39, to engage it in compensating block 53 and to remove it from enclosure 39 after the inspection method described below has been completed.

A moving arrangement 35 also comprises a sensor 61 for measuring the rotation of rod 3 connected to computerized system 37. This sensor 61 comprises for example a wheel bearing against rod 3 which is driven in rotation by rod 3 when it turns.

Computerized system 37 comprises a computer which itself comprises one or more processors, storage arrangement, input/output arrangement and if appropriate a display arrangement. In the example illustrated, it comprises a microcomputer which in particular comprises a screen 63, a central unit 65 and a keyboard 67.

A program is stored in computer 37 and in association with an image processing library is used to perform the non-destructive method of test. Such image processing libraries are currently commercially available.

The steps used by the non-destructive method of test are as follows.

Computer 37 first of all detects and analyses any porosity present in circular weld bead 15. Such porosity is detected through reduced absorption of X-rays, and thus by lighter regions.

In order to do this an area IA1C of acquired image IA1 corresponding to the area of rod 3 containing weld bead 15 is selected as illustrated in FIG. 4. The letter C indicates that this area relates to weld bead 15.

Figure 5:
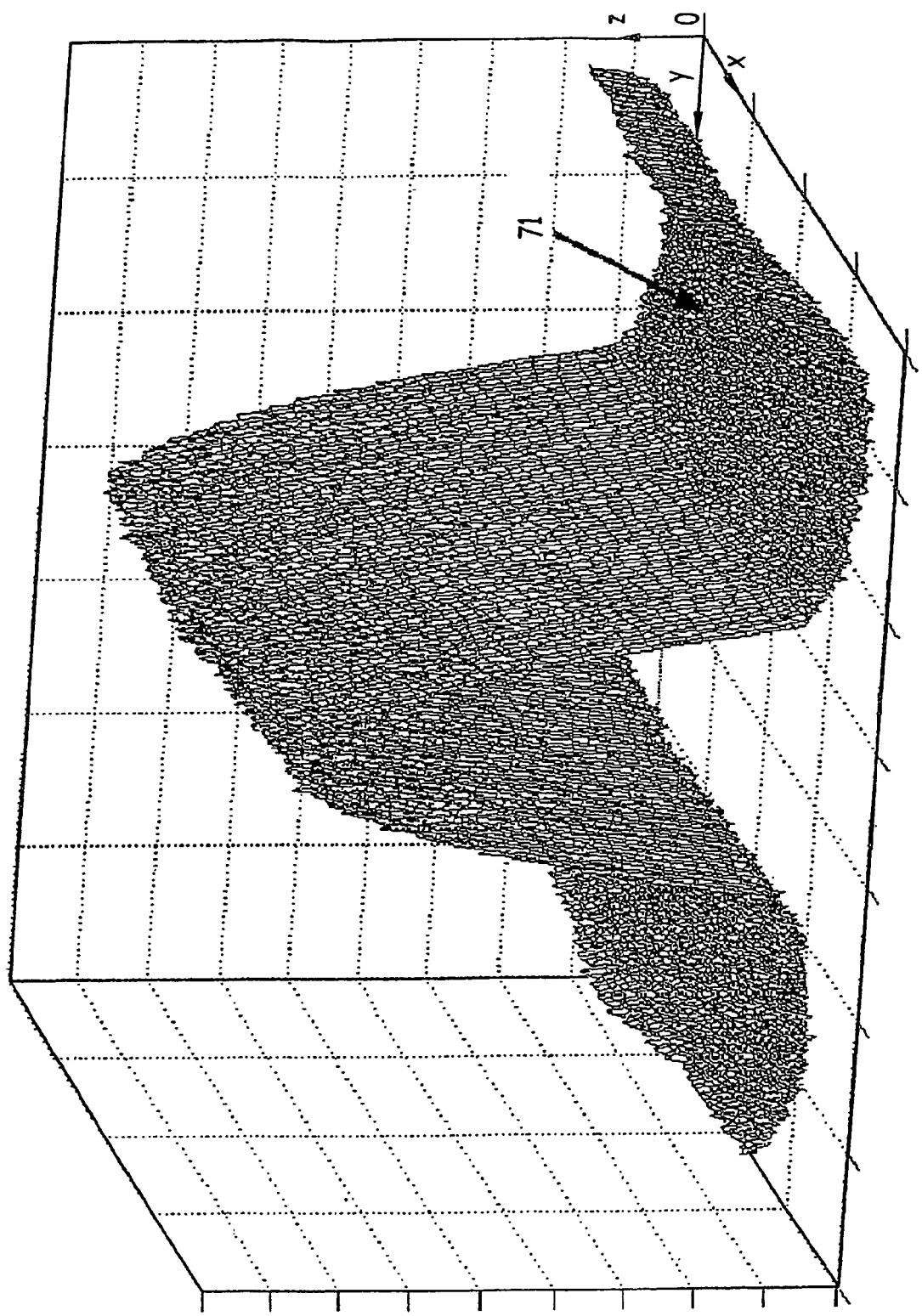
FIG. 5 is a three-dimensional diagram illustrating the grey levels of the area of the image in FIG. 4 corresponding to the circular weld bead.

FIG. 5 shows the different levels of grey in area IA1C. These grey levels are plotted on the Oz axis of the Oxyz grid illustrated in the figure. The Ox and Oy axes are also shown in FIG. 4.

As will be apparent later, weld bead 15 has porosity 71 which cannot be detected in the image obtained.

Figure 6:
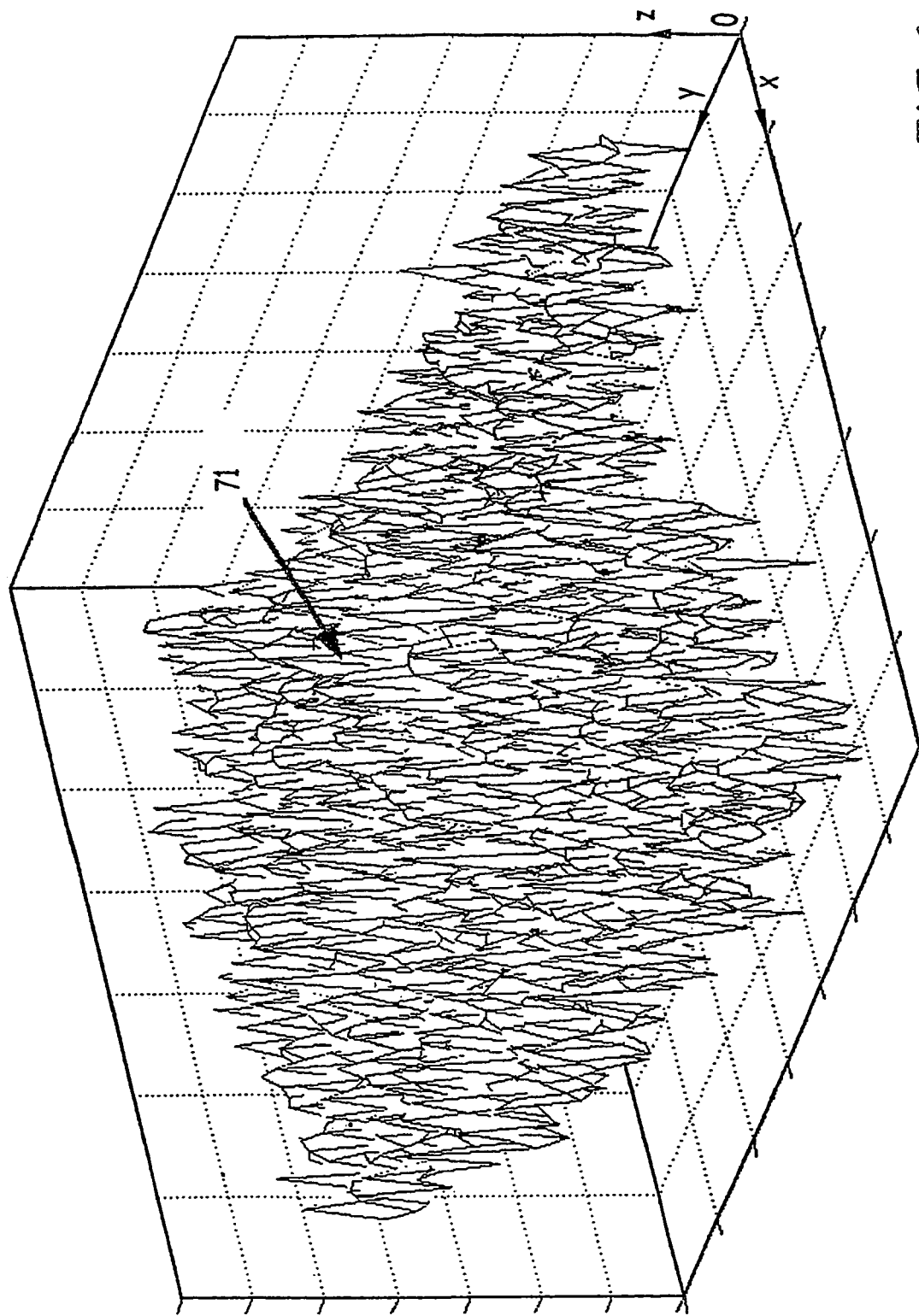
FIG. 6 is a partial magnified view of a FIG. 5 corresponding to a region in which there is porosity.

FIG. 6 is an enlarged part of FIG. 5 where porosity 71 is located.

In order to be able to detect this porosity 71, a reference image IR1C corresponding to a bead 15 which has no defects will be created by digitally processing area IA1C.

In order to do this area IA1C will be subjected to a smoothing operation through a convolver g which is a square of pixels of side n, n being a whole number, preferably between 3 and 9.

Convolver g is centred in its central pixel.

The operation to which area IA1C is subjected therefore corresponds to the following formula:

$$I \times g(x, y) = \sum_{v=-\infty}^{+\infty} \sum_{w=-\infty}^{+\infty} g(v, w) \times I(x - v, y - w)$$

In this formula and those which follow, I indicates the image undergoing processing.

This operation will therefore replace each pixel by the mean of the adjacent pixels present in the convolver centred on the pixel in question. For example with a convolver g having sides of 5 pixels, each pixel will be replaced by the mean of the pixel in question and the 24 adjacent pixels. Area IA1C obtained from the smoothing step is identified as IL1C.

Figure 7:
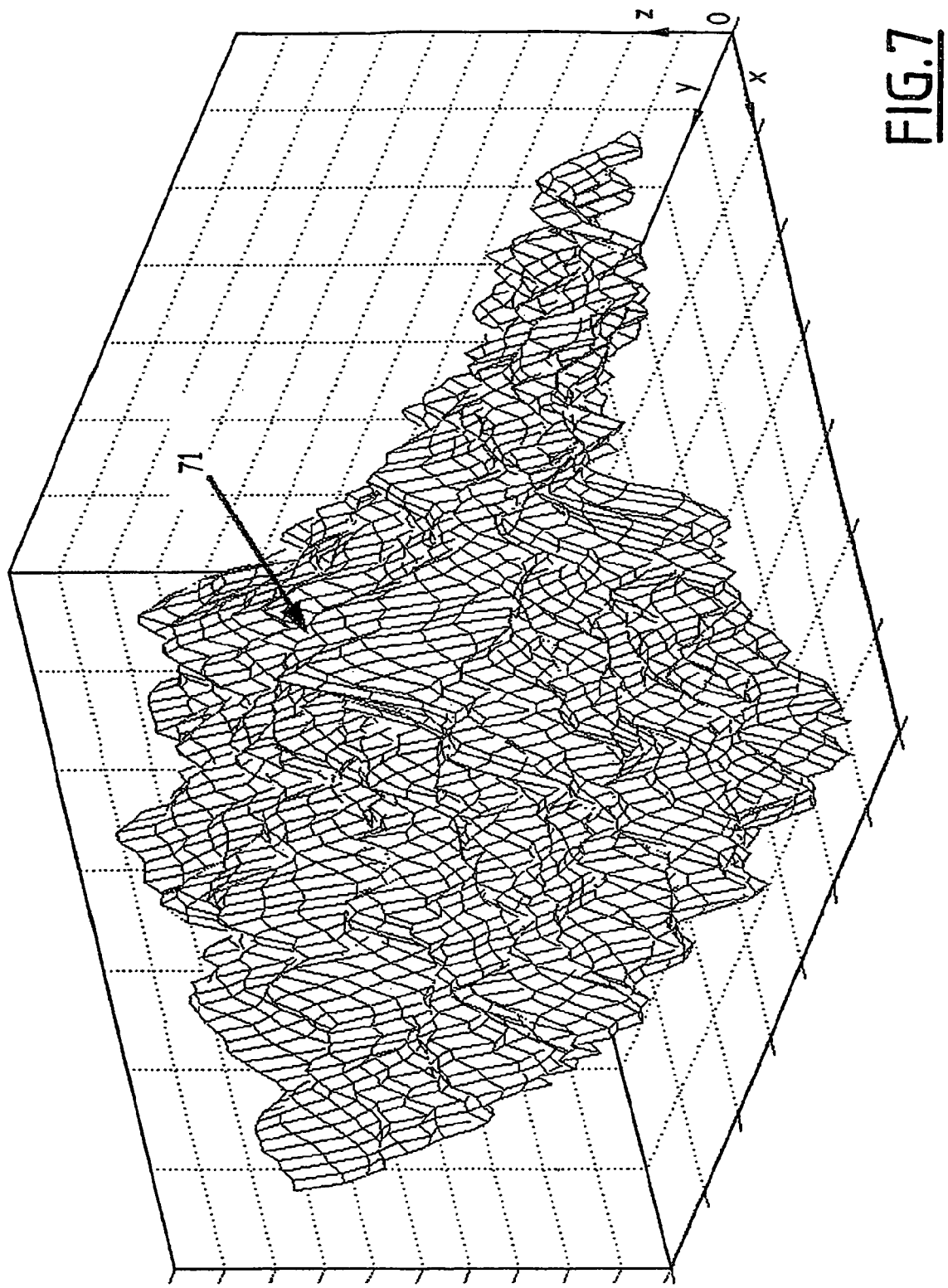
FIG. 7 is a view similar to that in FIG. 6 after smoothing.

FIG. 7 is a view similar to FIG. 6 at the end of the smoothing step.

Smoothed area IL1C is then subjected to opening by adding a structuring element h which is a segment parallel to the Ox axis centred on its central pixel.

This segment has a length of p pixels, p being a whole number, preferably between 5 and 21.

Opening by addition is erosion by a structuring element followed by dilation, that is dilation by the same structuring element.

Opening by addition of structuring element h will therefore be defined by the formula:

$$(I \ominus h) \oplus h$$

The erosion corresponds to the first part of this formula and consists of passing structuring element h over the area IL1C like a convolver, and allocating the minimum value to the central pixel.

Thus, the erosion corresponds to the formula:

$$(I \ominus h)(x) = \text{Min}(I(v))$$
$$v \in h(x)$$

Further details about mathematical morphological operations such as opening, "top hats", and image processing operations such as smoothing can be found in the work of J. Serra:

"Image Analysis and Mathematical Morphology" Ac. Press, Vol. 1 (1982), Vol. 2 (1988).

Figure 8:
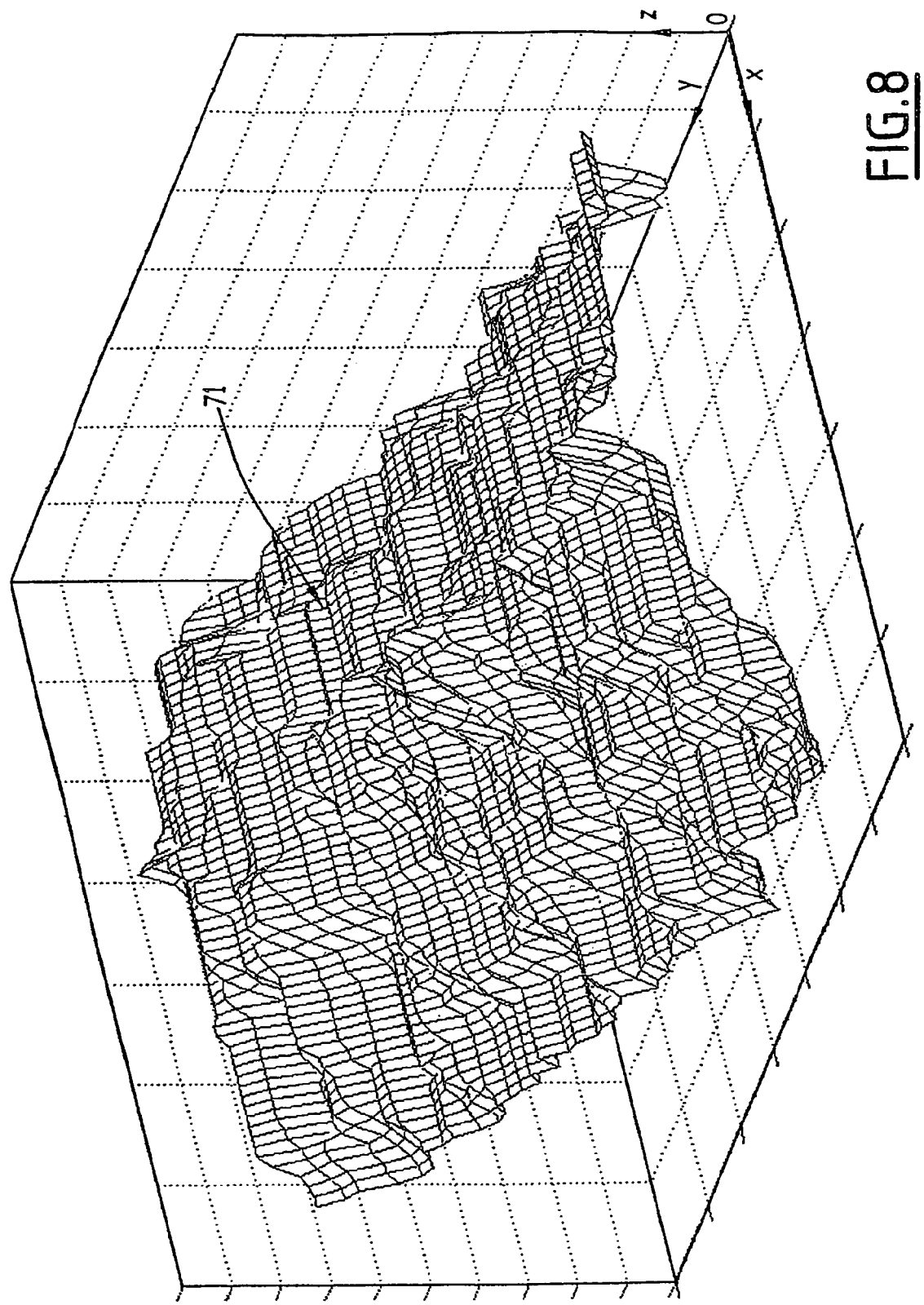
FIG. 8 is a view similar to that in FIG. 6 after erosion.

FIG. 8 corresponds to FIG. 6 after this erosion operation. The area processed is then identified as IE1c.

Figure 9:
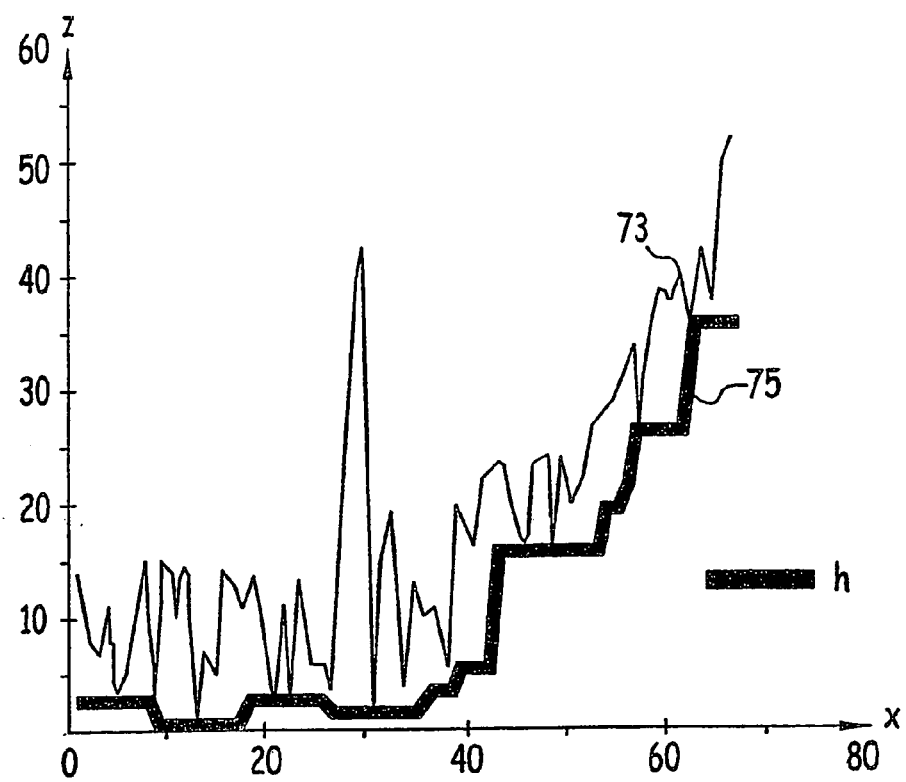
FIG. 9 is a diagram illustrating the effect of erosion on a graph.

FIG. 9 illustrates diagrammatically and in general the effect of such erosion produced on the changes in the grey levels of an image along the Ox axis.

Graph 73 corresponds to an image prior to erosion and graph 75 to an image after erosion.

Erosion therefore maintains the background of the image while eliminating the grey level peaks whose width is less than that of the structuring member.

Dilation, which is the second part of the opening operation, is designed to restore the grey levels in the image to where they were before the erosion.

Dilation consists of passing structural element h over the image, like a convolver, and allocating the maximum value to the central pixel in accordance with the formula:

$$(I \oplus h)(x) = \text{Max}(I(v))$$
$$v \in g(x)$$

Figure 10:
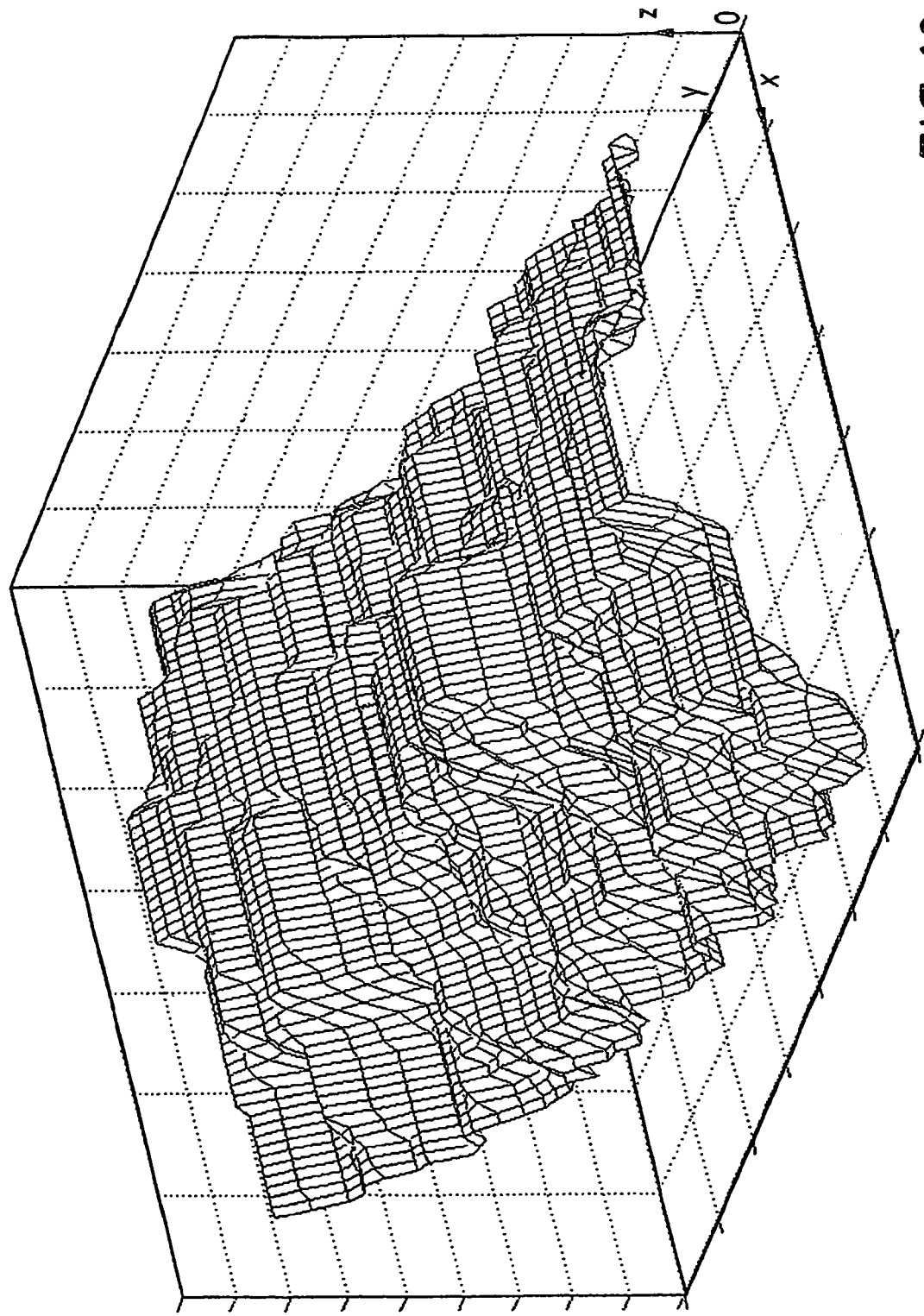
FIG. 10 is a view similar to that in FIG. 6 after dilation.

As illustrated in FIG. 10, the grey levels in the image return to those of the smoothed image, but porosity 71 has disappeared.

Figure 11:
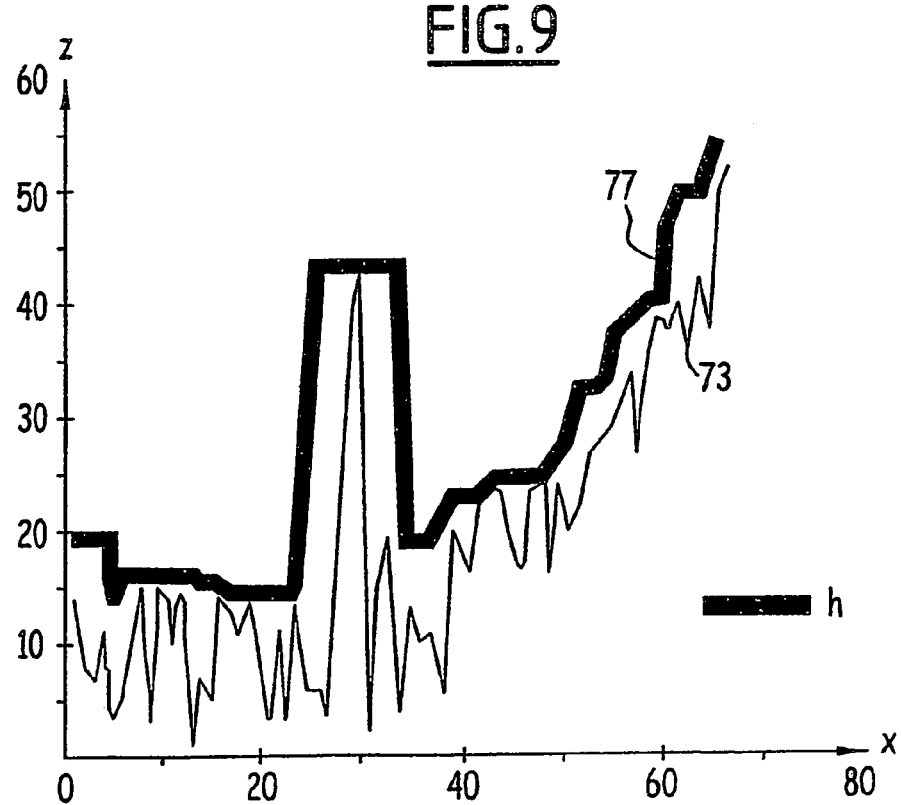
FIG. 11 is a view similar to that in FIG. 9 illustrating the effect of dilation.

In FIG. 11, graph 77 corresponds to an image after dilation.

The image obtained after this opening operation through addition therefore constitutes a reference image IR1C because any defects have been processed out.

It will be noted that the position and dimensions of the various parts of rod 3 in this image correspond to those of area IA1C in the image obtained because it has been obtained by digital processing of the latter.

Then in order to detect and analyse any defects the smoothed image IL1C will be compared with the reference image IR1C.

The following operation will be performed in order to do this:

$$\frac{ILR1C - IR1C}{IR1C} \times K$$

This means that the grey level of the pixel corresponding to the reference image IR1C will be subtracted from the grey level of each pixel in image IL1C, and then divided by the grey level of the pixel in the reference image IR1C and finally multiplied by the coefficient K and the result so obtained will be reallocated to the pixel in question.

The first part of this formula corresponds to a so-called "logarithmic" subtraction. In fact the reference image IR1C is not only subtracted from the smoothed image IL1C, but this difference is also divided by one of the terms in the subtraction.

Further information on logarithmic subtractions can be found in the publication:

"A model for logarithmic image processing" by Michel Jourlin and Jean-Charles Pinoli—Journal of Microscopy, Vol. 149, Pt 1, January 1988, pp. 21-35 (The Royal Microscopical Society).

Such logarithmic subtraction can be used to take into account the absorption of X-rays by the material.

In fact a defect seen through little material will have a tendency to appear larger than the same defect when seen through more material. This so-called "logarithmic" subtraction therefore makes it possible to compensate for this effect.

The multiplier coefficient K is a parameter representing camera 33 and may substantially correspond to the dynamic or image resolution acquired by camera 33, that is the maximum value of the light intensity.

This multiplication by coefficient K makes it possible to reduce the grey levels to those of the image IA1C.

Figure 12:
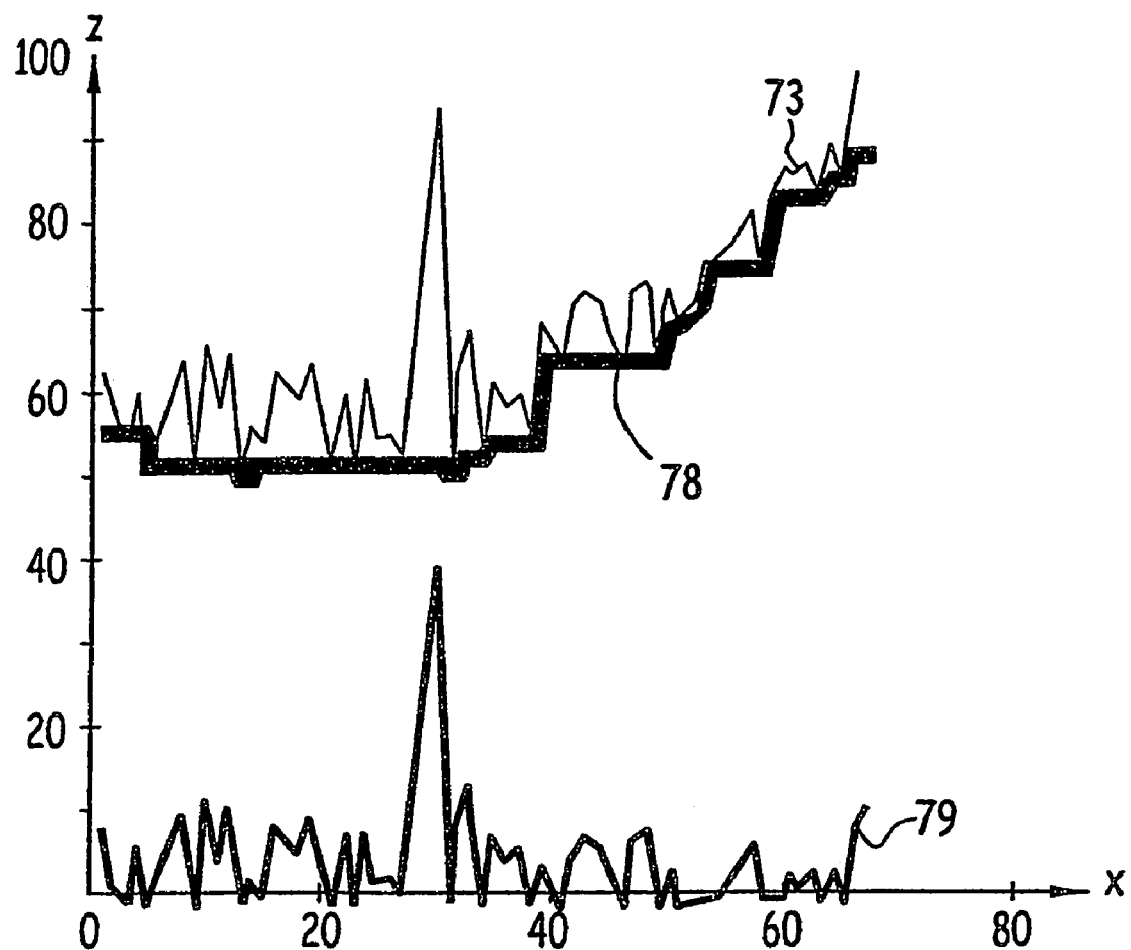
FIG. 12 is a view similar to that in FIG. 9 illustrating the effect of a "top hat"

Combination of the operations of opening by adding structuring element h and then subtraction may in fact be similar to a "top-hat", although in such "top-hats" subtraction is not "logarithmic". In FIG. 12, which illustrates the effect of such a "top-hat" in a general way, graph 78 corresponding to graph 73 after opening and graph 79 corresponds to the subtraction of graph 78 from the original graph 73.

Figure 13:
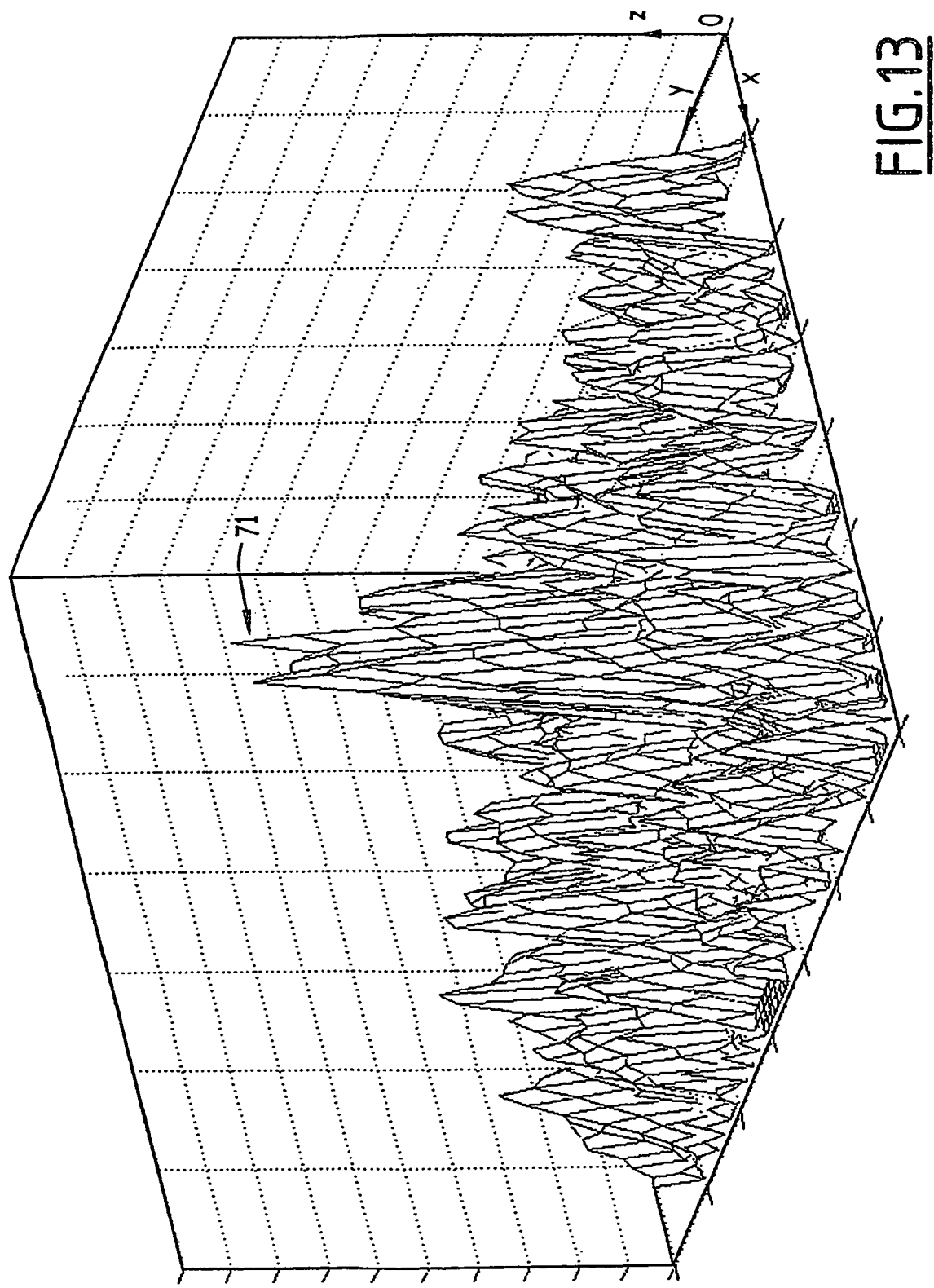
FIG. 13 is a view similar to that in FIG. 6 after logarithmic subtraction.

FIG. 13 corresponds to FIG. 6 after the "top-hat" processing applied by computer 37. The image is then called IS1C.

The "top-hat" operation has therefore made porosity 71 prominent.

Image IS1C is then subjected to an averaging operation, that is to say a smoothing, through a convolver j which is also a square, but of larger dimensions than convolver g. Thus this square has for example a square of pixels of side q, q being a whole number, preferably between 5 and 21.

Figure 14:
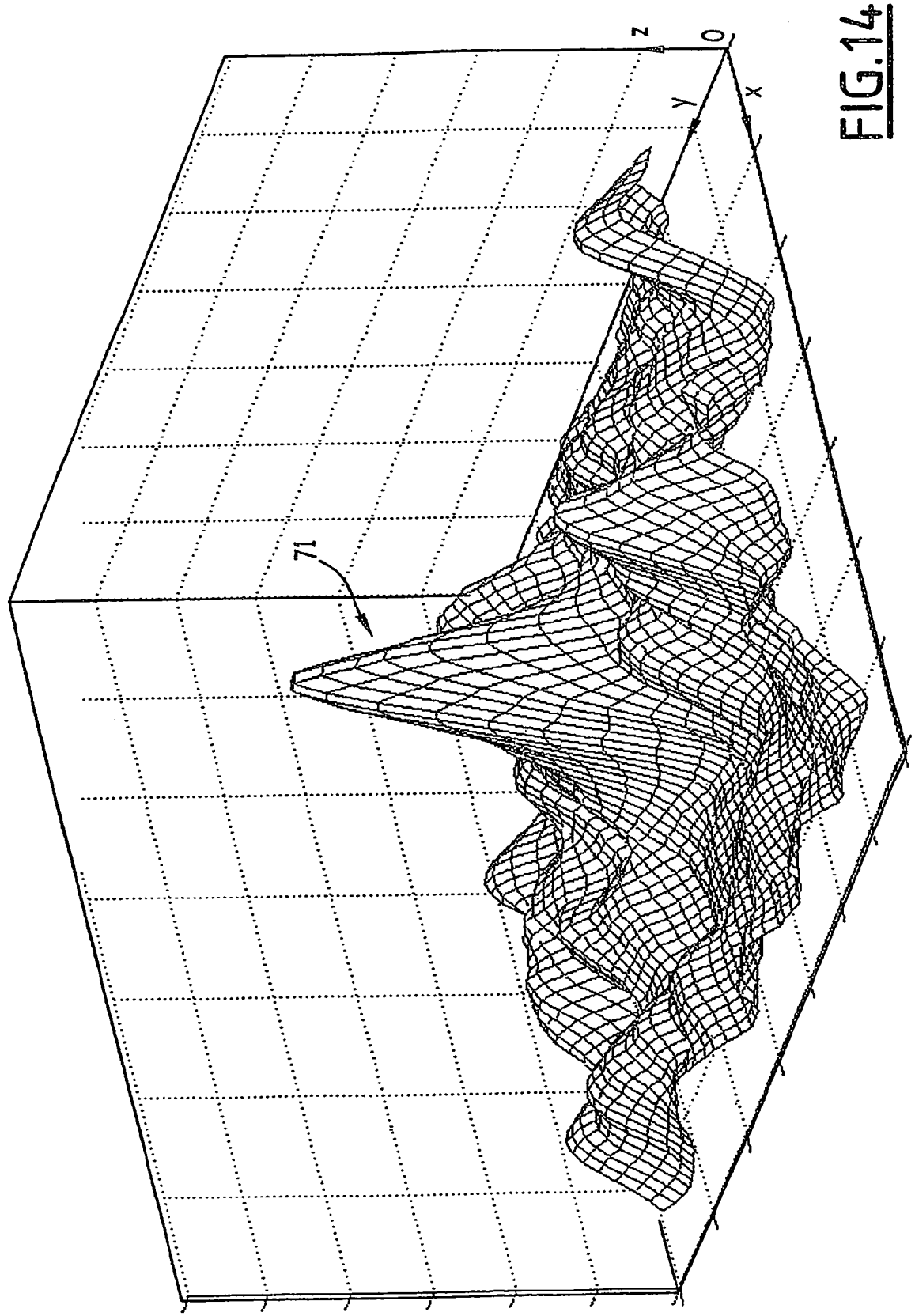
FIG. 14 is a view similar to that in FIG. 6 after further smoothing.

As can be seen in FIG. 14 illustrating the image after the second smoothing step, porosity 71 becomes more compact and parasites are attenuated.

The image obtained is then called IM1CP. The letter P indicates that this image is intended for searching for porosity. Image IM1CP will then be subjected to a step of binarisation.

This step consists of displaying the pixels of the image whose grey level is below a specific digital threshold in white and displaying those whose grey level is above that threshold in black. The binarisation threshold, which may be modified, corresponds to the desired sensitivity of analysis.

Figure 15:
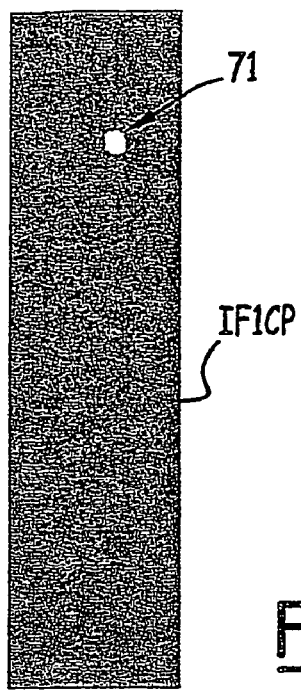
FIG. 15 illustrates the image of the area selected after these various processes.

The final image resulting from this processing thus appears as illustrated in FIG. 15 and is designated IF1CP. Porosity 71 appears there in the form of a white patch or singularity.

Computer 37 then detects and examines the defects in final image IF1CP.

In order to do this computer 37 uses the singularity or log-searching tool in the image processing library which also determines the characteristics of the singularities in the image IF1CP, that is the porosity detected in this way.

In particular, computer 37 calculates the positions of the porosities and their diameters.

Computer 37 then causes rod 3 to be rotated through an angle of 120°, acquires an image IA2 and then proceeds with all the operations previously described in its area IA2C, as a result of which a second view IF2CP of porosity 71 is obtained. Here the FIG. 2 means that these are images relating to the second viewpoint.

Finally, computer 37 again causes rod 3 to rotate through 120° about its longitudinal axis L and acquires an image IA3 in this new position, the area IA3C of which it processes in the manner indicated above.

Computer 37 then proceeds to reconstruct the defect or defects detected, in the case in point porosity 71.

Figure 16:
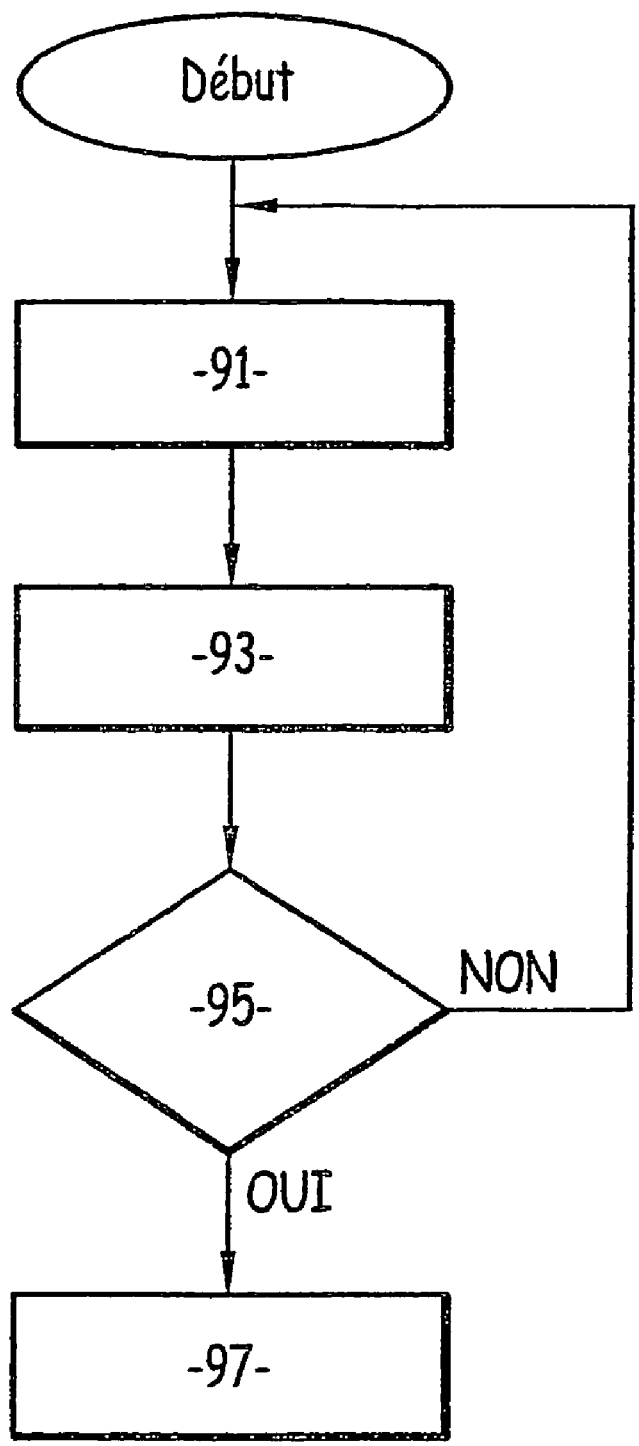
FIG. 16 is an organization chart illustrating the steps used to reconstruct detected porosity.

The operations then performed by computer 37 are illustrated by the organization chart in FIG. 16.

In a first step 91 computer 37 selects porosity detected in the view IF1CP.

Using the coordinates of the porosity in view IF1CP computer 37 then calculates the coordinates which it might occupy in views IF2CP and IF3CP. This is the purpose of step 93.

Then in step 95 computer 37 checks whether the calculated coordinates correspond to those of the porosity actually detected in views IF2CP and IF3CP. If this is not the case the porosity detected in only view IF1CP is ignored and step 91 is performed using another porosity in view IF1CP.

If the result in comparison step 95 is positive, the porosity will then have been detected in at least two views and computer 37 can determine its precise coordinates and evaluate its actual diameter in step 97.

If the porosity is only detected in two views, the actual diameter is calculated for example from a formula of the type $Am^2+Bm+c$ where m is the mean of the diameters determined in the two views in which the porosity was detected.

If the porosity is detected in three views, the actual diameter is calculated using a formula of the type $A'm+B'$ where m is the mean diameter of the diameters determined in the three views IF1CP, IF2CP and IF3CP.

Thus computer 37 knows the precise positions of the porosities detected and has determined their actual diameters.

It is then in a position to illustrate these porosities in transverse cross-section.

Figure 17:
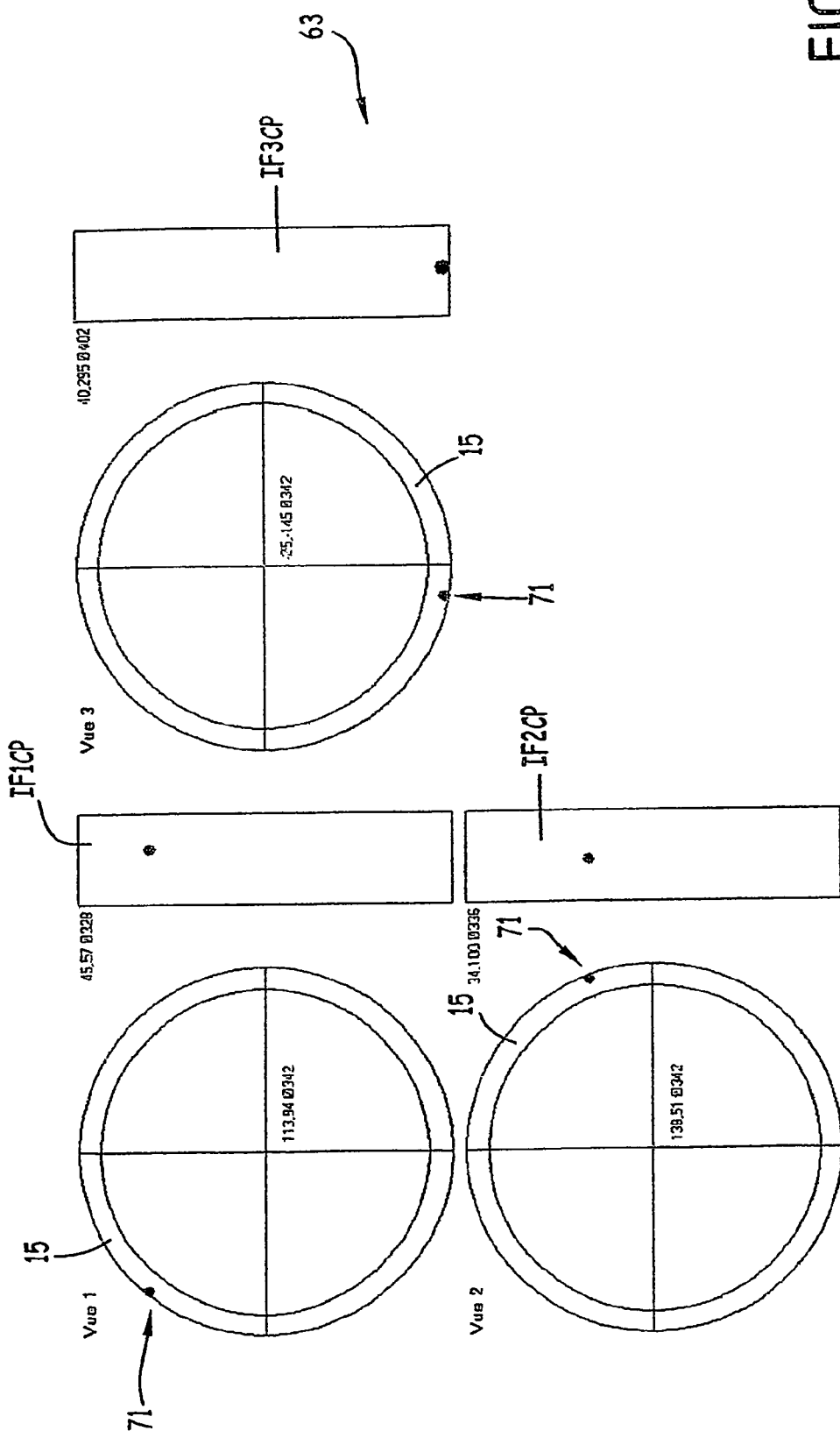
FIG. 17 is a view illustrating the computer screen display of the facility after porosities have been reconstructed.

This is illustrated by FIG. 17 which illustrates the display of weld bead 15 on screen 63 in transverse cross-sections and in which only porosity 71 detected is displayed. Each of these transverse sections corresponds to a viewing angle.

Finally computer 37 can compare the diameters of the porosities detected with a maximum permitted value, and compare the sum of these diameters with a threshold value. If the values measured and the sum are less than the maximum value and the threshold value, rod 3 is declared to be conforming as regards the porosities in weld bead 15.

Facility 1 described above makes it then possible to detect and analyse lack of penetration in weld bead 15.

It will not be forgotten that this lack of penetration corresponds to inadequate local radial thickness of bead 15 so that the seal between plug 9 in question and sheath 5 may be compromised.

Such lack of penetration, which corresponds to a lack of material, appears in the form of a lighter patch on the radiographs.

In order to detect such lack of penetration, computer 37 processes images IA1C, IA2C and IA3C.

The processing operations are the same as those described above for the search for porosity, except that the second step of smoothing or averaging step is carried out by a convolver k which is both larger than in the case when searching for porosities and also lies along the Oy direction, that is transverse to the longitudinal axis L.

Thus it may be a rectangle centred on its central pixel. This rectangle may for example have r pixels along the side in the Ox direction, r being a whole number between 5 and 15, and s pixels along the side in the Oy direction, s being a whole number for example between 10 and 20.

The use of a convolver along the Oy direction makes it possible to give prominence to defects having such a shape, which is the case for lack of penetration which extends angularly somewhat, but not the case for porosity, which is similar to bubbles.

Likewise the binarisation threshold, that is to say the threshold grey level above which the pixels are displayed white, is higher than when searching for porosity.

Figure 18:
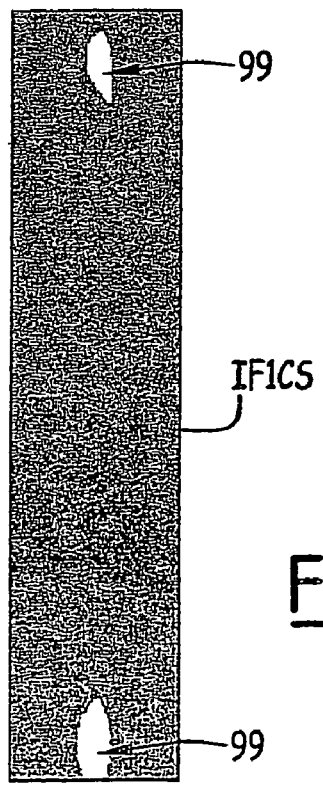
FIG. 18 is a view similar to FIG. 15 after the various steps of image processing have been applied in order to detect lack of penetration in the circular weld bead.

The final images obtained after these steps in processing are identified as IF1CS, IF2CS, IF3CS. FIG. 18 illustrates the image IF1CS. This image is the product of a succession of images corresponding to each of the processing steps, namely images IA1C, IL1C, IE1C, ID1C, IS1C, IM1CS and IFCS.

The letter S indicates that these images are being used to search for lack of penetration.

The coordinates and surfaces of the singularities 99 revealed, in this case lack of penetration, can also be determined and displayed through the image processing library. There are two instances of lack of penetration 99 in image IF1CS.

The same steps are applied using images IF2CS and IF3CS.

Computer 37 can then calculate a score relating to lack of penetration in weld bead 15. This score may be the sum of all the surface areas of the instances of lack of penetration 99 detected, which may be weighted.

Comparison of this lack of penetration score with a threshold score makes it possible to make a decision about the conformance of rod 3 examined as regards lack of penetration in weld bead 15.

Figure 19:
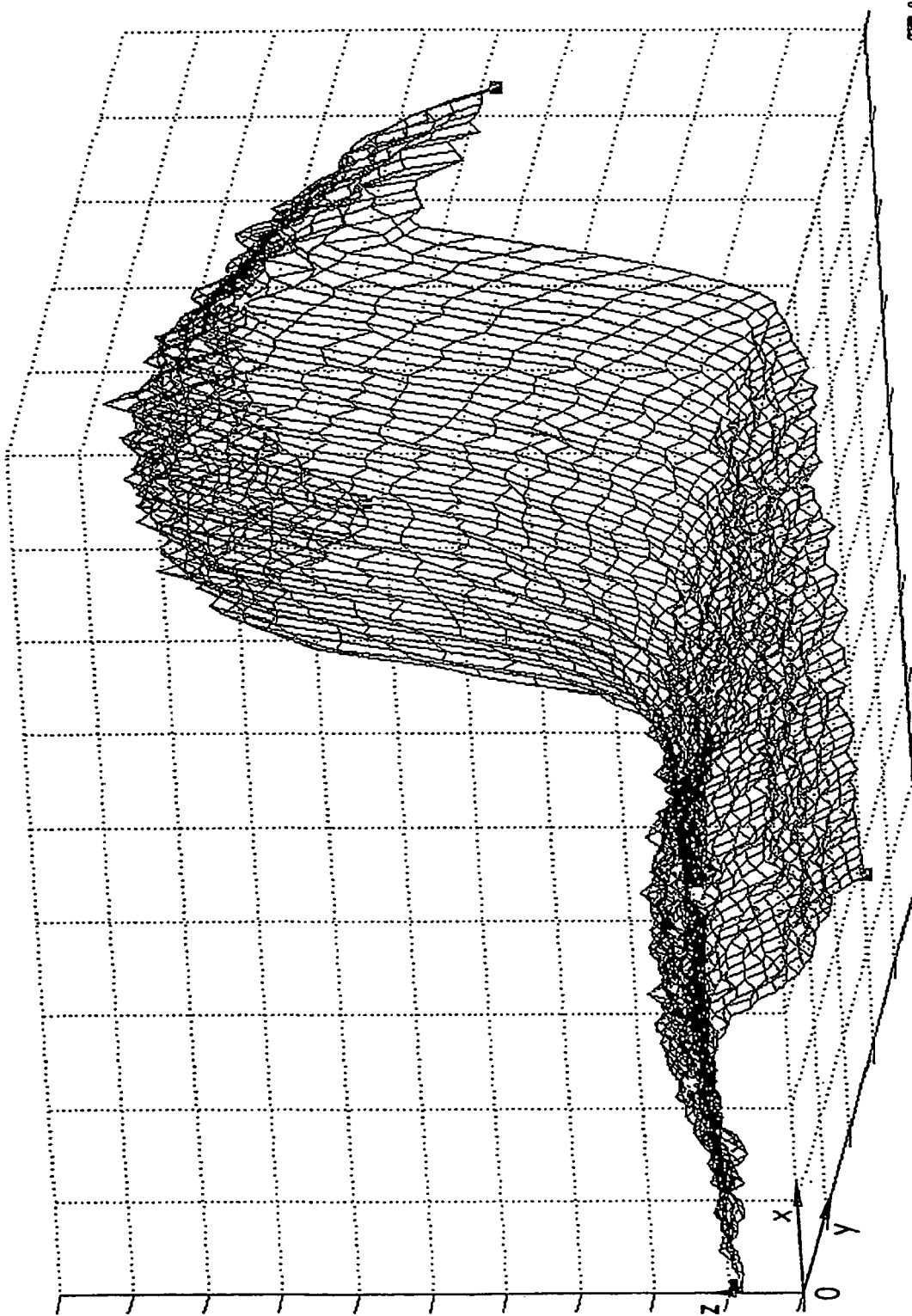
FIG. 19 is a three-dimensional diagram illustrating the grey levels for the area of the image in FIG. 4 corresponding to the spot weld sealing the filling channel in the top plug.

Facility 1 can then be used to check for potential leaks in spot weld 27 on filling channel 19 of sheath 5. In order to do this an area IA1Q of acquired image IA1 is selected as illustrated in FIG. 4. The letter Q indicates that this area relates to checking for potential leaks in line with seal weld location 23. FIG. 19 illustrates the grey levels in this area IA1Q.

Finally this image IA1Q is subjected to a smoothing operation through a convolver I which is for example a square of t adjacent pixels centred on its central pixel, t being a whole number of for example between 3 and 9.

The size of this convolver is small so as to modify image IA1Q as little as possible. The image resulting from this processing is identified as IL1Q.

Image IL1Q is then subjected to a step of projection along the Ox axis and reconstruction.

More specifically, this projection and reconstruction step consists of allocating the mean value of the grey levels of the pixels in that column to a pixel in each column extending along the Oy axis.

This processing emphasises the background of image IL1Q and therefore processes out any local longitudinal lack of penetration at the spot weld.

Figure 20:
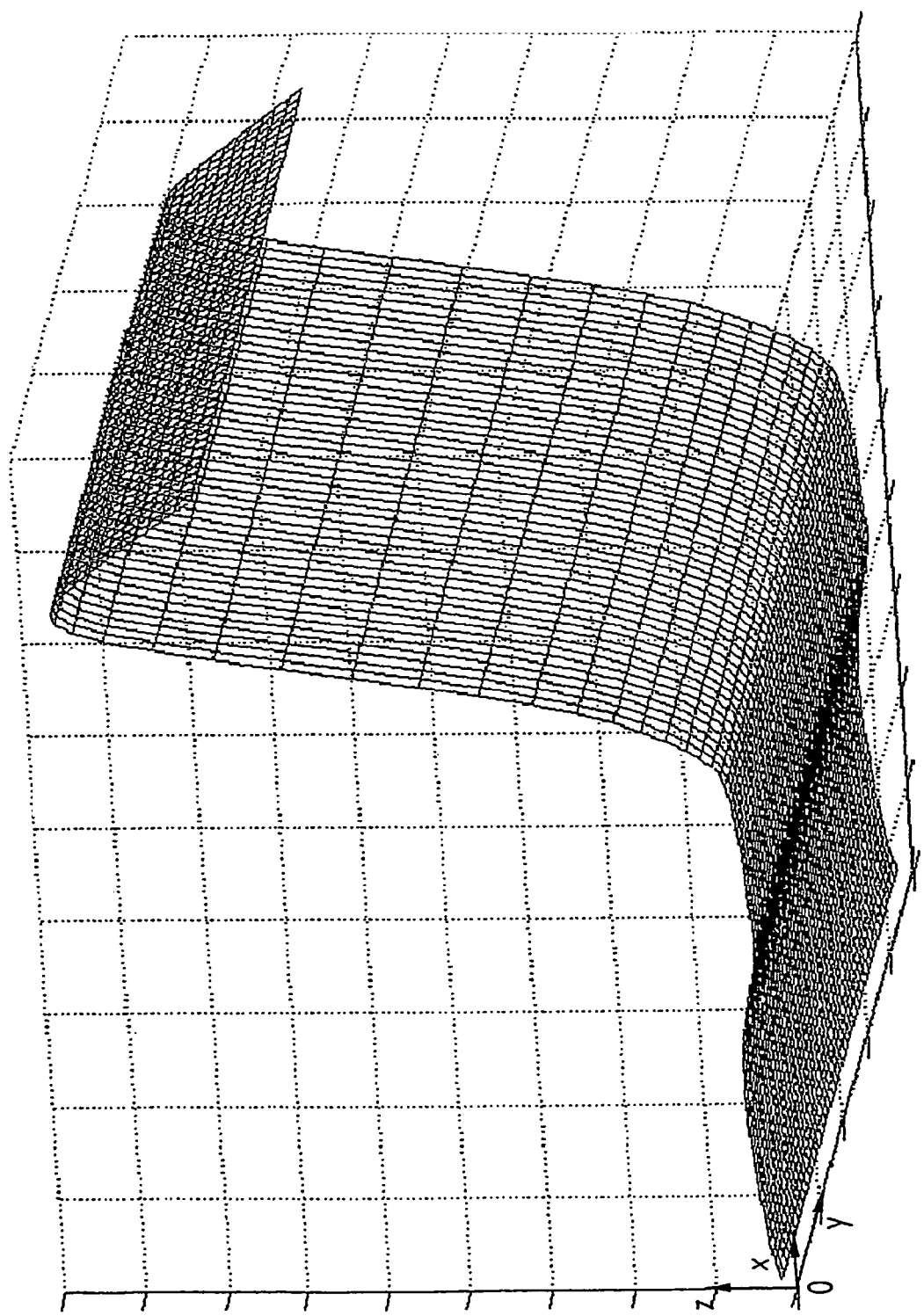
FIG. 20 is a figure similar to FIG. 19 after projection and reconstruction.

The image so obtained is a reference image IR1Q whose grey levels vary only along the Ox direction, as illustrated in FIG. 20.

Reference image IR1Q is then subtracted from smoothed image IL1Q. This is a simple IL1Q-IR1Q subtraction and not a logarithmic subtraction.

Figure 21:
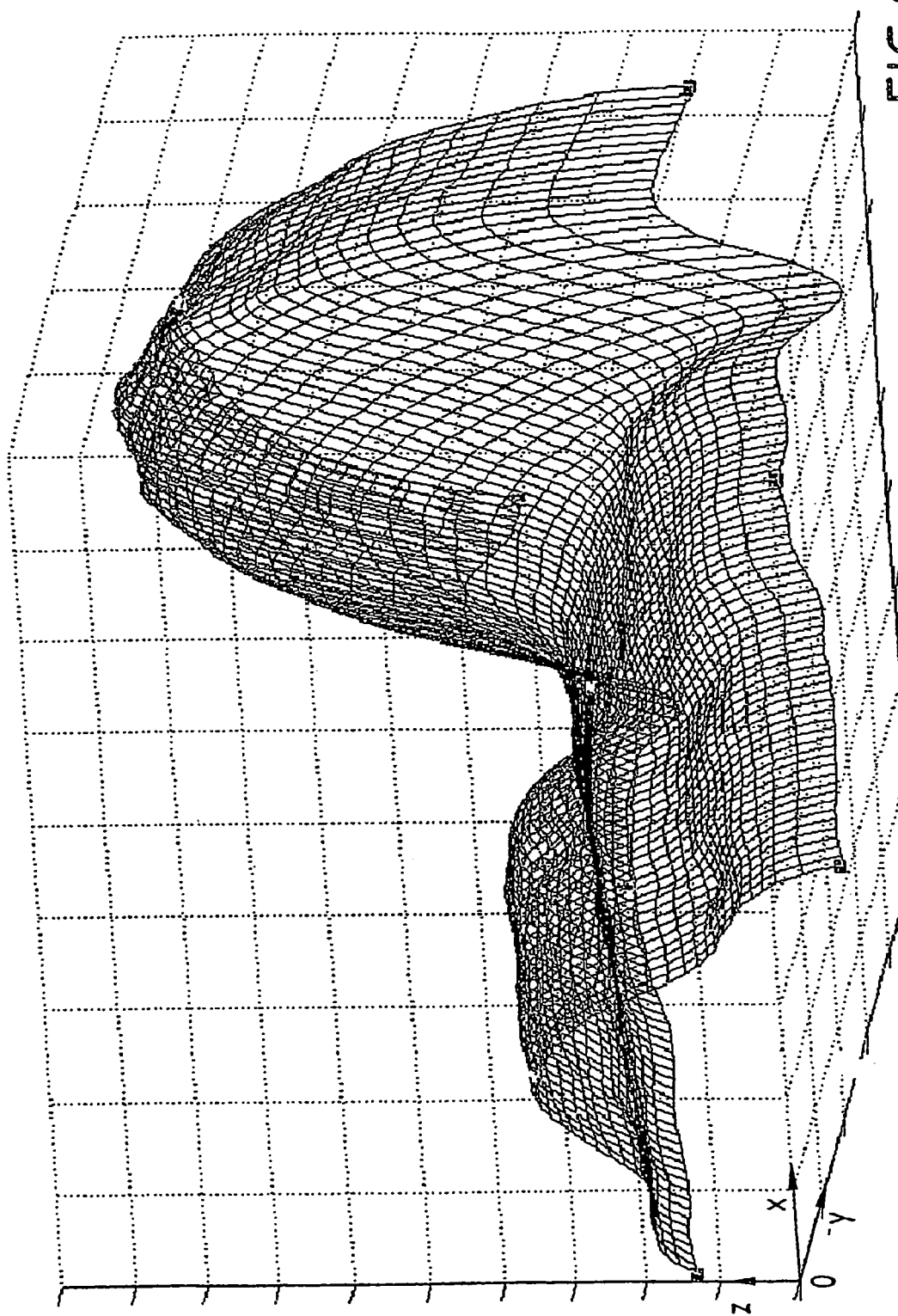
FIG. 21 is a view similar to FIG. 19 after subtraction.

FIG. 21 illustrates the grey levels after this operation.

Image IS1Q obtained from the subtraction is then binarised to obtain a final image IF1Q in which all the pixels having a grey level less than a threshold value are allocated the value zero and all the others are allocated the maximum grey level value.

Figure 22:
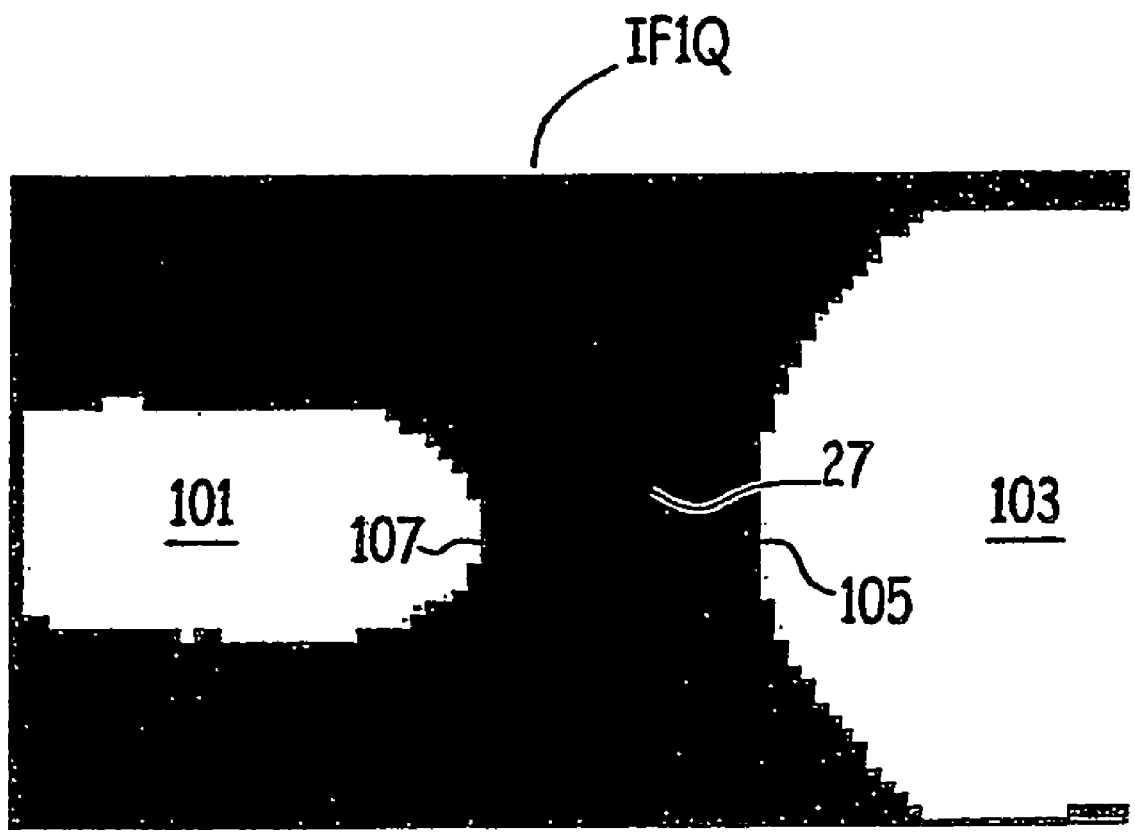
FIG. 22 represents the image of the area corresponding to the spot weld after the various steps of processing have been applied.

FIG. 22 illustrates image IF1Q. Region 101 of channel 19 beneath spot weld 27 can be seen on the left and cavity 103 formed beneath spot weld 27 can be seen on the right. It will be noted that in the case of TIG welding spot weld 27 does not form a cavity but has a convex external surface.

Computer 37 will then detect areas 101 or 103 using the singularities search tool in the image processing library. If no area or just a single area crossing image IA1Q horizontally is detected, seal weld 23 is regarded as being not welded and rod 3 is considered to be non-conforming. This latter situation in fact means that areas 101 or 103 join up. If two areas 101 and 103 are detected, computer 37 calculates the distance between these two areas 101 and 103 which appear white in image IF1C, using the image treatment library. In order to do this the library for example traces the edge 105 of cavity 103 on image IF1C and then constructs edge 107 of area 101.

In order to do this computer 37 runs across image IF1Q towards the right on each line, starting from the left-hand edge of image IF1Q, until it finds edge 105.

Computer 37 then runs along the line in question in the reverse direction until it detects the first white pixel. If it detects such a white pixel, this is the location of edge 107 of area 101 on the line in question. If it detects no white pixel, which in fact corresponds to the situation where only one area 103 is present on the right of image IF1Q, computer 37 regards edge 107 as the left-hand edge of image IF1Q.

Thus, proceeding line by line, computer 37 determines the coordinates of the points of the edges of 105 and 107 of the two light areas 101 and 103.

Then starting from all these coordinates computer 37 calculates the minimum distance between these edges 105 and 107, a distance which corresponds to the axial penetration of spot weld 27 into channel 19.

Computer 37 will then proceed in the same way for views IA2 and IA3 and provide final images IF2Q and IF3Q from areas IA2Q and IA3Q, and then determine the axial penetration of spot weld 27 into channel 19 for each of these views.

Computer 37 finally calculates the actual axial penetration of spot weld 27 as the mean of the axial penetrations determined from the three views IF1Q, IF2Q and IF3Q. It then compares this value with a threshold value, below which it considers that spot weld 27 does not sufficiently penetrate channel 19 to ensure that rod 3 is leaktight.

It will also be noted that images IA1Q, IA2Q and IA3Q can be subjected to processing for searching for porosity, this processing being similar to that described previously for weld bead 15.

Finally facility 1 also makes it possible to determine the presence of tungsten inclusions when bead 15 and/or spot weld 17 are carried out by TIG welding.

In fact these inclusions appear as darker areas on the digital radiographs acquired by camera 33. Using processing similar to that described for porosity or lack of penetration, these defects can then be detected and analysed and a decision can be made on the basis of predetermined conformance criteria.

Instead of the operation of opening by addition an operation of closing through a structuring element h is then used. This operation is defined by the formula $$(I \oplus h) \ominus h$$

Such closure makes it possible to eliminate negative peaks and thus to form satisfactory reference images.

Structuring element h is then preferably similar to that described previously.

It will be noted that the defects sought appear in the form of negative peaks in the grey levels, binarisation being inverted with respect to that described previously. As a variant it is the subtraction operation which can be inverted, that is to say the smoothed image is subtracted from the eroded image, the resultant being divided by the eroded image and multiplied by coefficient K.

Figure 23:
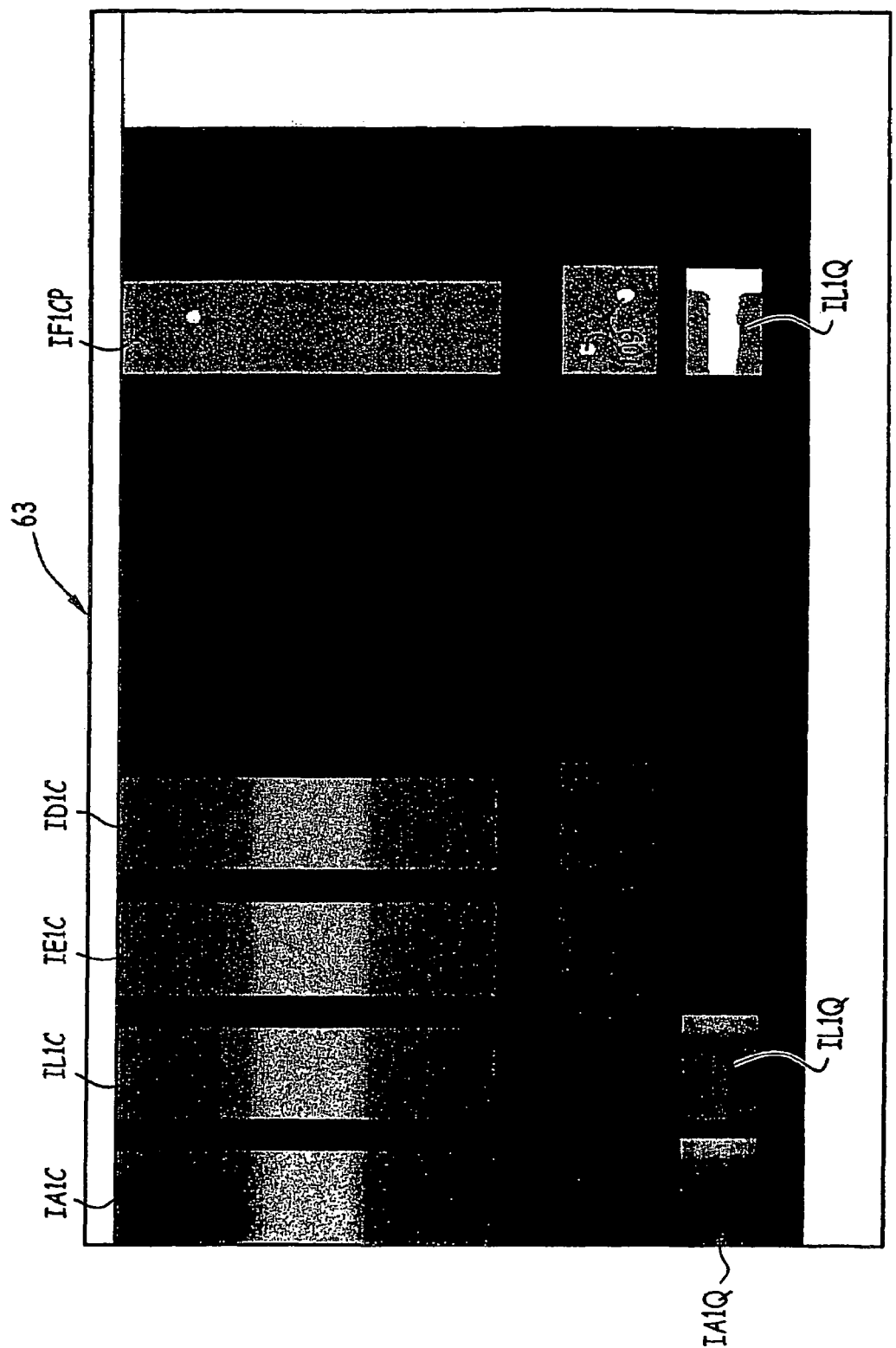
FIGS. 23 to 25 are views illustrating the display on the computer screen of the facility in FIG. 1 after the non-destructive method of test has been carried out.

It is then possible to display all the images obtained and processed for each viewing angle on screen 63. FIG. 23 thus illustrates the display on screen 63 for a first viewing angle.

The upper sequence of images corresponds to the images relating to the search for porosity, namely IA1C, IL1C, IE1C, ID1C, IS1C, IM1CP and IF1CP. Images IS1C and IM1CP are certainly present between images ID1C and IF1CP but are not visible because of their low grey levels.

The intermediate sequence of images corresponds to an image area IA1 in which the holes of the image quality indicator (IQI) 51 can be seen. These images have been subjected to exactly the same processing as image IA1C, including the operations of determining the positions and diameters of singularities.

The bottom sequence of images corresponds to the sequence of images relating to spot weld 27, namely IA1Q, IL1Q, IR1Q, IS1Q and IF1Q. It will be noted that in the example in FIG. 23 seal weld 23 is not welded.

The bottom part of screen 63 can provide information relating to the positions and diameter of porosities 71 detected, the positions and diameters of patches 109 detected in the area corresponding to the image quality indicator (IQI) 51, and the axial penetration of spot weld 27 for the viewing angle in question.

Figure 24:
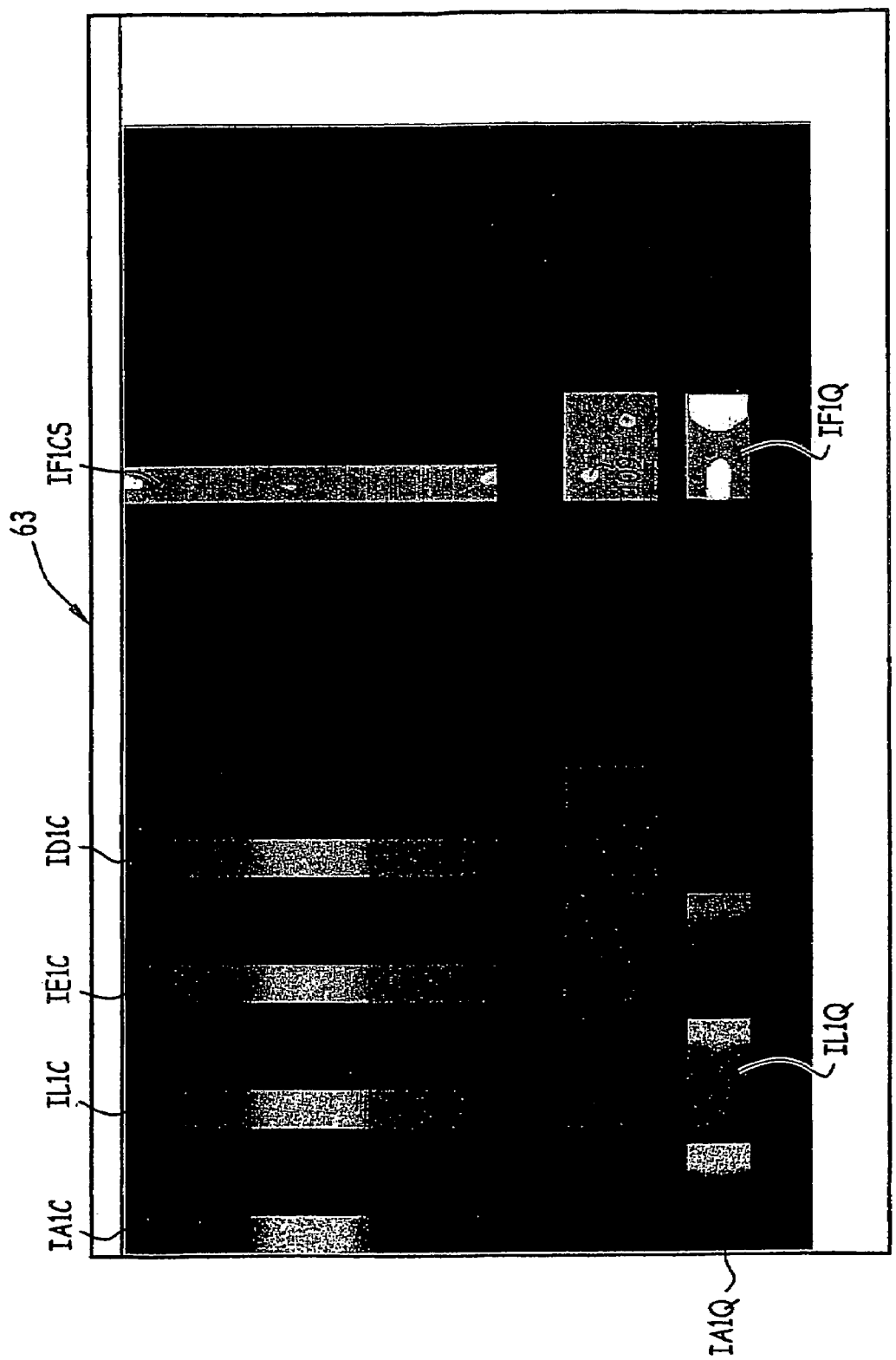

The dimensions of the patches detected in the images corresponding to the IQI can be used to check the reliability of the measurements made. Screen 63 can also display the sequence of images corresponding to the search for lack of penetration in its top part. This is illustrated in FIG. 24.

Figure 25:
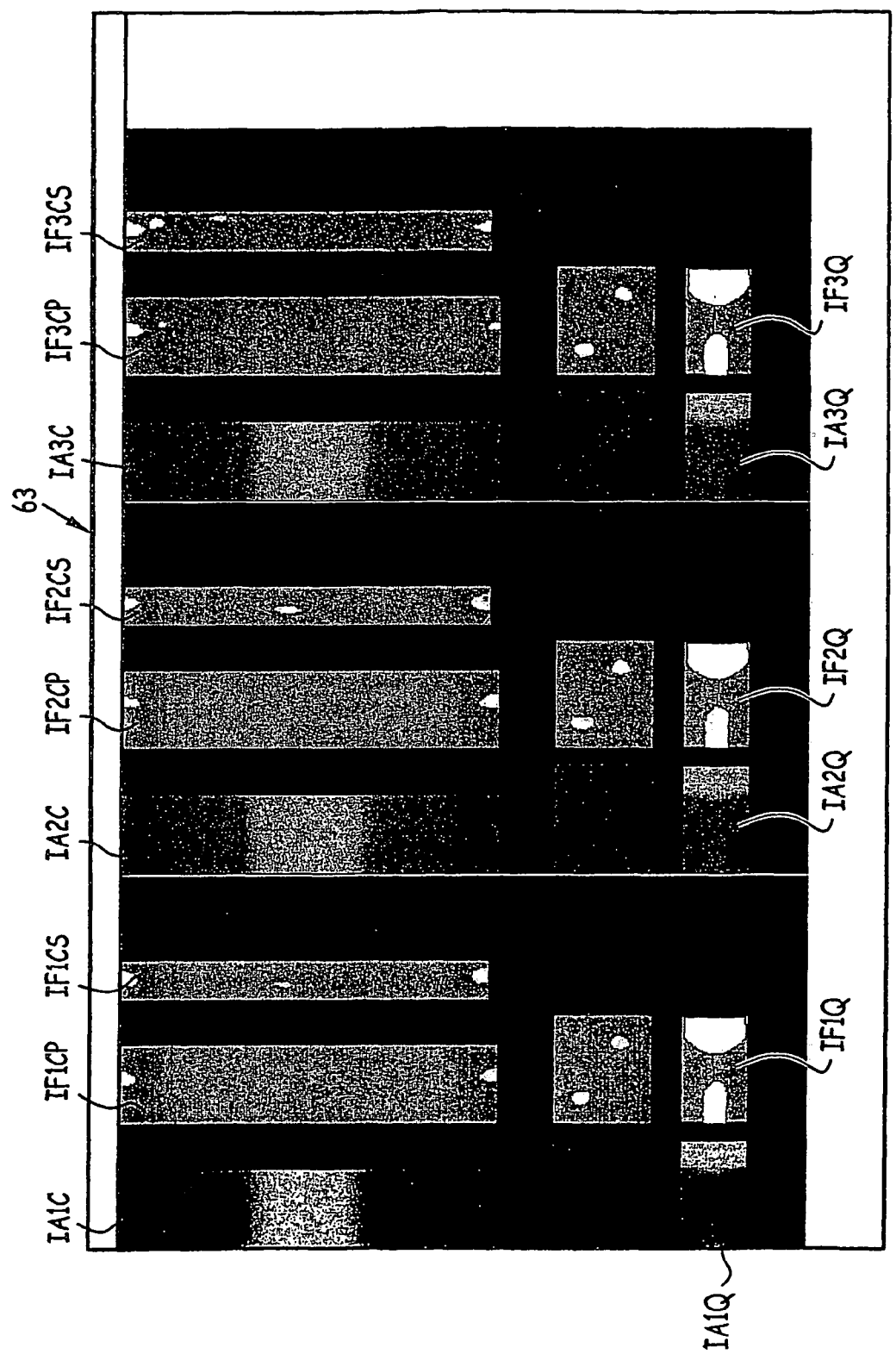

Finally, and as illustrated in FIG. 25, the screen can also display simultaneously:

in a top part, images IA1C, IA2C, IA3C, IF1CP, IF2CP, IF3CP, IF1CS, IF2CS, IF3CS relating to the inspection of bead 15, in an intermediate region, the initial and final images for the three views relating to the quality indicator IQI, in a bottom region, the images IA1Q, IA2Q, IA3Q, IF1Q, IF2Q and IF3Q relating to the inspection of spot weld 27.

Thus facility 1 has made it possible to automatically determine whether top plug 9 of rod 3 has any porosity or lack of penetration in bead 15 or a potential leak at spot weld 27, and any tungsten inclusions which would justify the rejection of rod 3. The procedure is then performed in a similar way for bottom plug 9.

It has been established that the non-destructive method of test described is particularly quick to carry out because it makes it possible to provide a verdict on each plug 9 in less than 26 seconds. The number of rods 3 improperly rejected is also reduced.

Furthermore the method described can be used to detect and characterise defects separately and to reconstruct some of them, that is to determine their precise positions and some of their characteristics.

This reliability and this speed of operation is due to construction of the reference images, in particular IR1C, IR2C, IR3C, IR1Q, IR2Q and IR3Q from the acquired images IA1C, IA2C, IA3C, IA1Q, IA2Q and IA3Q.

In fact this makes it possible to ensure precise correspondence between the contours on these images, which simplifies the processing necessary in order to then isolate the defects sought.

More generally other digital processing of acquired images may be carried out in order to form reference images. In the case of weld bead 25 opening by addition is preferably used and this when combined with the following subtraction operation forms a "top-hat".

The use of a structuring element h in the form of a segment parallel to the L axis has proved to be particularly advantageous. In fact such a structuring element makes it possible to limit the aberrations introduced into the images as a result of the presence of channel 19.

More generally structuring element h may not be a segment but may have a form elongated along longitudinal axis L. It may thus comprise a rectangle.

More generally, the above principles, namely the creation of a reference image by the processing of an acquired image of the item under inspection can be used to inspect components of nuclear reactors other than nuclear fuel rods, in particular their welds.

The invention claimed is:

1. A method for non-destructive testing of an element of a nuclear reactor, comprising:
    acquiring a radiographic digital image of at least one area in the element of the nuclear reactor;
    creating a reference image through digital processing of the radiographic image obtained; and
    comparing the radiographic digital image obtained, one of processed and unprocessed, with the reference image to detect a presence of defects.

2. The method according to claim 1, wherein the element is part of a nuclear fuel assembly.

3. The method according to claim 2, wherein the element is a nuclear fuel rod extending along a longitudinal axis and comprising a sheath sealed by top and bottom plugs and containing a nuclear fuel.

4. The method according to claim 3, wherein the area comprises a weld bead between one of the plugs and the sheath.

5. The method according to claim 3, wherein the area comprises a spot weld sealing off a channel passing through the plug.

6. The method according to claim 5, wherein the step of creating a reference image through digital processing of the radiographic image obtained comprises a substep of projecting the image along the longitudinal axis and reconstructing the image from projection along the axis.

7. The method according to claim 6, further comprising:
    smoothing the image acquired by a convolver prior to the substep of projecting the image along the longitudinal axis and reconstructing the image from projection along the axis.

8. The method according to claim 7, wherein the convolver is a square of t adjacent pixels, wherein t is a whole number.

9. The method according to claim 6, wherein comparing the radiographic digital image obtained, one of processed and unprocessed, with the reference image to detect a presence of defects comprises a substep of subtracting the reference image from the image obtained.

10. The method according to claim 9, further comprising:
    binarization of the image after the substep of subtracting the reference image from the image obtained.

11. The method according to claim 6 further comprising: determining a minimal axial thickness of the spot weld.

12. The method according to claim 11, wherein the method is performed for more than one viewing angles, the method further comprising:
    calculating a mean of minimum thicknesses determined for several viewing angles and comparing the mean of minimum thicknesses with a threshold value to make a decision on whether the element conforms with predetermined manufacturing criteria.

13. The method according to claim 1, further comprising:
    automatically detecting and determining characteristics of a region of the image produced in comparing the radiographic digital image obtained, one of processed and unprocessed, with the reference image to detect a presence of defects corresponding to a defect.

14. The method according to claim 13, wherein one of the characteristics is a position of the defect detected in the image.

15. The method according to claim 13, wherein one of the characteristics is representative of a dimension of the defect.

16. The method according to claim 15, wherein the method is performed for more than one viewing angles, the method further comprising:
    summing representative characteristics of the dimension determined for more than one viewing angles and comparing the sum with a threshold value in order to obtain a decision on whether the element conforms with predetermined manufacturing criteria.

17. The method according to claim 13, wherein the method is performed for more than one viewing angles.

18. The method according to claim 17, wherein one of the characteristics is a position of the defect detected in the image and one of the characteristics is representative of a dimension of the defect, the method further comprising:
    reconstructing defects detected in the images corresponding to the more than one viewing angles.

19. The method according to claim 18, wherein the step of reconstructing defects detected in the images corresponding to the more than one viewing angles comprises a first substep of determining positions which a defect detected in a first image corresponding to a first viewing angle occupies in a second image corresponding to a second viewing angle, a second substep of comparing positions so determined with the positions of the defect actually detected in the second image to determine whether the defect has been detected in the second image, and upon detection of the defect in the second image, performing a third substep of calculating a dimension of the defect from representative characteristics of the dimensions of the defect determined in the first and second image.

20. A method for non-destructive testing of an element of a nuclear reactor, comprising:
   acquiring a radiographic digital image of at least one area in the element of the nuclear reactor;
   creating a reference image through digital processing of the radiographic image obtained; and
   comparing the radiographic digital image obtained, one of processed and unprocessed, with the reference image to detect a presence of defects, wherein the step of creating a reference image through digital processing of the radiographic image obtained comprises a substep of one of opening and closing the image by adding a structuring element.

21. The method according to claim 20, wherein the element is a nuclear fuel rod extending along a longitudinal axis and the structuring element has a shape that is elongated along the longitudinal axis of the rod.

22. The method according to claim 21, wherein the structuring element is a segment of p pixels, wherein p is a whole number that is not zero.

23. The method according to claim 21, wherein the nuclear fuel rod comprises a sheath sealed by top and bottom plugs and containing a nuclear fuel, a weld bead being between one of the plugs and the sheath and wherein a defect that has to be detected is one of porosity and lack of penetration of the weld bead and the substep is opening the image by adding the structuring element.

24. The method according to claim 21, wherein a defect that has to be detected is a tungsten inclusion and the substep is closing the image by adding the structuring element.

25. The method according to claim 20, wherein the step of creating a reference image through digital processing of the radiographic image obtained has a substep of smoothing the image through a convolver prior to the substep of one of opening and closing the image by adding a structuring element.

26. The method according to claim 25, wherein the convolver is a square of n adjacent pixels, wherein n is a whole number that is not zero.

27. A method for non-destructive testing of an element of a nuclear reactor, comprising:
   acquiring a radiographic digital image of at least one area in the element of the nuclear reactor;
   creating a reference image through digital processing of the radiographic image Obtained; and
   comparing the radiographic digital image obtained, one if processed and unprocessed, with the reference image to detect a presence of defects wherein the step of comparing the radiographic digital image obtained, one of processed and unprocessed, with the reference image to detect a presence of defects comprises a substep of calculating a difference between the acquired image that is one of processed and unprocessed, and the reference image and of dividing the difference by one of the radiographic image obtained, that is one of processed and unprocessed, and the reference image.

28. The method according to claim 27, wherein after the substep, the image is multiplied by a coefficient substantially corresponding to a maximum light intensity of a viewing device used to obtain the radiographic image.

29. The method according to claim 27, wherein after the substep, the image is smoothed using a convolver.

30. The method according to claim 29, wherein the convolver is a square of q adjacent pixels, wherein q is a whole number.

31. The method according to claim 29, wherein the convolver lies transversely with respect to a longitudinal axis extending along the element.

32. The method according to claim 27, further comprising:
   binarization of the image after the substep of calculating a difference between the acquired image that is one of processed and unprocessed, and the reference image and of dividing the difference by one of the radiographic image obtained, that is one of processed and unprocessed, and the reference image.

* * * * *